(12) United States Patent
Kolosov et al.

(10) Patent No.: US 7,302,830 B2
(45) Date of Patent: Dec. 4, 2007

(54) FLOW DETECTORS HAVING MECHANICAL OSCILLATORS, AND USE THEREOF IN FLOW CHARACTERIZATION SYSTEMS

(75) Inventors: Oleg Kolosov, San Jose, CA (US); Leonid Matsiev, San Jose, CA (US); Miroslav Petro, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 691 days.

(21) Appl. No.: 10/163,064

(22) Filed: Jun. 5, 2002

(65) Prior Publication Data

US 2003/0000291 A1 Jan. 2, 2003

Related U.S. Application Data

(60) Provisional application No. 60/296,638, filed on Jun. 6, 2001.

(51) Int. Cl.
*G01N 30/00* (2006.01)

(52) U.S. Cl. .................... 73/61.52; 73/53.01; 73/61.43; 73/61.41

(58) Field of Classification Search .............. 73/61.52, 73/61.43, 61.41, 53.01
See application file for complete search history.

(56) References Cited

U.S. PATENT DOCUMENTS

| | | | |
|---|---|---|---|
| 3,273,377 A | 9/1966 | Testerman et al. | |
| 3,622,968 A | 11/1971 | Silverman | |
| 3,710,275 A | 1/1973 | Tanaka et al. | |
| 3,718,032 A | 2/1973 | Gray | |
| 3,762,197 A | 10/1973 | Roof et al. | |
| 3,778,757 A | 12/1973 | Houston | |
| 3,902,365 A * | 9/1975 | Knauth | 73/861.03 |
| 3,903,732 A | 9/1975 | Rork et al. | |
| 3,921,622 A | 11/1975 | Cole | |
| 3,926,271 A | 12/1975 | Patashnick | |
| 4,103,224 A | 7/1978 | Taro et al. | |
| 4,145,922 A | 3/1979 | Estrada, Jr. et al. | |
| 4,312,228 A | 1/1982 | Wohltjen | |
| 4,342,936 A | 8/1982 | Marcus et al. | |
| 4,349,881 A * | 9/1982 | November et al. | 702/54 |
| 4,361,026 A | 11/1982 | Muller et al. | |

(Continued)

FOREIGN PATENT DOCUMENTS

DE 4424422 1/1996

(Continued)

OTHER PUBLICATIONS

Senstronics "Storm 50 Joint Pressure and Temperature Specifications".

(Continued)

*Primary Examiner*—Hezron Williams
*Assistant Examiner*—Rodney Frank
(74) *Attorney, Agent, or Firm*—Senniger Powers

(57) ABSTRACT

An improved system, device and method for characterizing a fluid sample that includes injecting a fluid sample into a mobile phase of a flow characterization system, and detecting a property of the fluid sample or of a component thereof with a flow detector comprising a mechanical resonator, preferably one that is operated at a frequency less than about 1 MHz, such as a tuning fork resonator.

25 Claims, 8 Drawing Sheets

U.S. PATENT DOCUMENTS

| | | | |
|---|---|---|---|
| 4,370,662 A | 1/1983 | Hou et al. | |
| 4,372,173 A * | 2/1983 | EerNisse et al. | 73/862.59 |
| 4,391,338 A | 7/1983 | Patashnick et al. | |
| 4,526,480 A | 7/1985 | Ward | |
| 4,535,620 A | 8/1985 | Cunnungham | |
| 4,543,829 A | 10/1985 | Lerch | |
| 4,549,427 A | 10/1985 | Kolesar, Jr. | |
| 4,596,697 A | 6/1986 | Ballato | |
| 4,602,505 A | 7/1986 | Kanda et al. | |
| 4,624,129 A | 11/1986 | Haynes | |
| 4,644,803 A | 2/1987 | Ward | |
| 4,696,181 A | 9/1987 | Rupprecht et al. | |
| 4,721,874 A | 1/1988 | Emmert | |
| 4,729,237 A | 3/1988 | Suzuki et al. | |
| 4,734,609 A | 3/1988 | Jasime | |
| 4,735,103 A * | 4/1988 | Mussard et al. | 73/862.59 |
| 4,741,200 A | 5/1988 | Hammerle | |
| 4,760,351 A | 7/1988 | Newell et al. | |
| 4,767,719 A | 8/1988 | Finlan | |
| 4,779,451 A | 10/1988 | Ezawa et al. | |
| 4,782,332 A | 11/1988 | Cipris et al. | |
| 4,783,987 A | 11/1988 | Hager et al. | |
| 4,802,370 A | 2/1989 | EerNisse et al. | |
| 4,802,384 A | 2/1989 | Schwarz et al. | |
| 4,812,698 A | 3/1989 | Chida et al. | |
| 4,862,384 A | 8/1989 | Bujard | |
| 4,890,480 A | 1/1990 | Young | |
| 4,893,496 A | 1/1990 | Bau et al. | |
| 4,904,978 A | 2/1990 | Barth et al. | |
| 4,910,523 A | 3/1990 | Huguenin et al. | |
| 4,922,745 A | 5/1990 | Rudkin et al. | |
| 4,970,492 A | 11/1990 | King | |
| 5,006,845 A | 4/1991 | Calcar et al. | |
| 5,179,028 A | 1/1993 | Vali et al. | |
| 5,191,791 A | 3/1993 | Gerardi et al. | |
| 5,201,215 A | 4/1993 | Granstaff et al. | |
| 5,204,529 A | 4/1993 | Diatschenko | |
| 5,224,174 A | 6/1993 | Schneider et al. | |
| 5,235,844 A * | 8/1993 | Bonne et al. | 73/24.01 |
| 5,253,530 A | 10/1993 | Letcher, III | |
| 5,283,037 A | 2/1994 | Baer et al. | |
| 5,296,374 A | 3/1994 | Culshaw et al. | |
| 5,306,644 A | 4/1994 | Myerholtz et al. | |
| 5,325,704 A | 7/1994 | Mariami et al. | |
| 5,332,961 A | 7/1994 | Hammerle | |
| 5,334,900 A | 8/1994 | Kawashima | |
| 5,338,416 A | 8/1994 | Mlcak et al. | |
| 5,357,964 A | 10/1994 | Spivey et al. | |
| 5,361,632 A | 11/1994 | Magnani | |
| 5,375,470 A | 12/1994 | Matsushima et al. | |
| 5,421,190 A | 6/1995 | Brandle et al. | |
| 5,434,650 A | 7/1995 | Nakahara et al. | |
| 5,435,170 A | 7/1995 | Voelker et al. | |
| 5,445,008 A | 8/1995 | Wachter et al. | |
| 5,454,045 A | 9/1995 | Perkins et al. | |
| 5,455,475 A | 10/1995 | Josse et al. | |
| 5,464,509 A | 11/1995 | Mlcak et al. | |
| 5,469,369 A | 11/1995 | Rose-Pehrsson et al. | |
| 5,477,726 A | 12/1995 | Stabinger et al. | |
| 5,488,866 A | 2/1996 | Ravel et al. | |
| 5,524,477 A | 6/1996 | Wajid | |
| 5,524,636 A | 6/1996 | Sarvazyan et al. | |
| 5,531,091 A | 7/1996 | Gademann et al. | |
| 5,533,402 A | 7/1996 | Sarvazyan et al. | |
| 5,571,401 A | 11/1996 | Lewis et al. | |
| 5,571,952 A | 11/1996 | Kauzlarich | |
| 5,604,441 A | 2/1997 | Freese et al. | |
| 5,622,223 A | 4/1997 | Vasquez | |
| 5,653,939 A | 8/1997 | Hollis et al. | |
| 5,670,709 A | 9/1997 | Gallagher | |
| 5,698,089 A | 12/1997 | Lewis et al. | |
| 5,705,399 A | 1/1998 | Larue | |
| 5,734,098 A | 3/1998 | Kraus et al. | |
| 5,741,961 A | 4/1998 | Martin et al. | |
| 5,741,962 A | 4/1998 | Birchak et al. | |
| 5,744,902 A | 4/1998 | Vig | |
| 5,770,038 A | 6/1998 | Iwama et al. | |
| 5,776,359 A | 7/1998 | Schultz et al. | |
| 5,777,210 A | 7/1998 | Voelker et al. | |
| 5,789,665 A | 8/1998 | Voelker et al. | |
| 5,792,938 A | 8/1998 | Gokhfeld | |
| 5,796,001 A * | 8/1998 | Greiff et al. | 73/504.16 |
| 5,798,452 A | 8/1998 | Martin et al. | |
| 5,818,731 A | 10/1998 | Mittal et al. | |
| 5,827,952 A | 10/1998 | Mansure et al. | |
| 5,852,229 A | 12/1998 | Josse et al. | |
| 5,885,849 A | 3/1999 | Di Stephano et al. | |
| 5,889,351 A | 3/1999 | Okumura et al. | |
| 5,915,499 A | 6/1999 | Few | |
| 5,918,354 A * | 7/1999 | Ikegami et al. | 29/25.35 |
| 5,959,297 A | 9/1999 | Weinberg et al. | |
| 5,985,356 A | 11/1999 | Schultz et al. | |
| 6,023,961 A | 2/2000 | Discenzo et al. | |
| 6,034,775 A | 3/2000 | McFarland et al. | |
| 6,041,642 A | 3/2000 | Duncan | |
| 6,044,694 A | 4/2000 | Anderson et al. | |
| 6,126,311 A | 10/2000 | Schuh | |
| 6,151,123 A | 11/2000 | Nielsen | |
| 6,155,098 A | 12/2000 | Shapiro et al. | |
| 6,157,449 A | 12/2000 | Hajduk | |
| 6,175,409 B1 | 1/2001 | Nielsen et al. | |
| 6,176,323 B1 | 1/2001 | Weirich et al. | |
| 6,182,499 B1 * | 2/2001 | McFarland et al. | 73/24.06 |
| 6,223,589 B1 | 5/2001 | Dickert et al. | |
| 6,247,354 B1 | 6/2001 | Vig et al. | |
| 6,260,407 B1 | 7/2001 | Petro et al. | |
| 6,260,408 B1 | 7/2001 | Vig et al. | |
| 6,265,226 B1 * | 7/2001 | Petro et al. | 436/180 |
| 6,269,686 B1 | 8/2001 | Hahn et al. | |
| 6,275,137 B1 | 8/2001 | Doppalapudi et al. | |
| 6,286,363 B1 | 9/2001 | Discenzo | |
| 6,294,388 B1 | 9/2001 | Petro et al. | |
| 6,296,771 B1 | 10/2001 | Miroslav | |
| 6,306,358 B1 | 10/2001 | Yamamoto | |
| 6,306,658 B1 * | 10/2001 | Turner et al. | 436/37 |
| 6,311,549 B1 | 11/2001 | Thundat et al. | |
| 6,326,739 B1 * | 12/2001 | MacLennan et al. | 315/248 |
| 6,327,890 B1 | 12/2001 | Galipeau et al. | |
| 6,332,567 B1 * | 12/2001 | Ikegami et al. | 228/179.1 |
| 6,336,353 B2 * | 1/2002 | Matsiev et al. | 73/24.06 |
| 6,371,640 B1 | 4/2002 | Hajduk | |
| 6,393,895 B1 * | 5/2002 | Matsiev et al. | 73/24.06 |
| 6,401,519 B1 * | 6/2002 | McFarland et al. | 73/24.06 |
| 6,407,479 B1 | 6/2002 | Moellendorf et al. | |
| 6,412,131 B1 | 7/2002 | Zhao et al. | |
| 6,416,663 B1 * | 7/2002 | Miroslav et al. | 210/198.2 |
| 6,441,716 B1 | 8/2002 | Doppalapudi et al. | |
| 6,455,316 B1 * | 9/2002 | Turner et al. | 436/37 |
| 6,456,096 B1 | 9/2002 | Ericson et al. | |
| 6,459,995 B1 | 10/2002 | Collister | |
| 6,494,079 B1 * | 12/2002 | Matsiev et al. | 73/24.05 |
| 6,509,749 B1 | 1/2003 | Buelna et al. | |
| 6,511,915 B2 | 1/2003 | Mlcak | |
| 6,519,034 B1 | 2/2003 | Engler et al. | |
| 6,535,001 B1 | 3/2003 | Wang | |
| 6,536,634 B2 | 3/2003 | Berndorfer et al. | |
| 6,545,392 B2 | 4/2003 | Kawauchi et al. | |
| 6,557,396 B2 | 5/2003 | Ismail et al. | |
| 6,564,126 B1 | 5/2003 | Lin et al. | |
| 6,626,025 B2 | 9/2003 | Potyrailo et al. | |
| 6,640,644 B1 | 11/2003 | Mireles et al. | |
| 6,644,095 B2 | 11/2003 | Van Mullekom et al. | |
| 6,661,162 B1 | 12/2003 | Nagai et al. | |
| 6,684,683 B2 * | 2/2004 | Potyrailo et al. | 73/24.06 |

| | | | |
|---|---|---|---|
| 2001/0010174 | A1 | 8/2001 | Matsiev et al. |
| 2002/0064649 | A1 | 5/2002 | Lembke et al. |
| 2002/0068488 | A1 | 6/2002 | Tuller et al. |
| 2002/0070841 | A1 | 6/2002 | Doppalapudi et al. |
| 2002/0074897 | A1 | 6/2002 | Ma et al. |
| 2002/0092340 | A1 | 7/2002 | Prater et al. |
| 2002/0113596 | A1 | 8/2002 | Horie et al. |
| 2002/0121132 | A1 | 9/2002 | Breed et al. |
| 2002/0137348 | A1 | 9/2002 | Mlcak |
| 2002/0148529 | A1 | 10/2002 | Berndorfer et al. |
| 2002/0162385 | A1 | 11/2002 | Ismail et al. |
| 2002/0162390 | A1 | 11/2002 | Ismail et al. |
| 2002/0178787 | A1 | 12/2002 | Matsiev et al. |
| 2002/0178805 | A1* | 12/2002 | DiFoggio et al. ........ 73/152.55 |
| 2002/0194906 | A1 | 12/2002 | Goodwin et al. |
| 2003/0000291 | A1 | 1/2003 | Kolosov et al. |
| 2003/0041653 | A1 | 3/2003 | Matsiev et al. |
| 2003/0041659 | A1 | 3/2003 | Marszalek et al. |
| 2003/0062910 | A1 | 4/2003 | Wang et al. |
| 2003/0083825 | A1 | 5/2003 | Berndorfer |
| 2003/0116497 | A1 | 6/2003 | Carlson et al. |
| 2003/0118078 | A1 | 6/2003 | Carlson et al. |
| 2003/0119060 | A1 | 6/2003 | Desrosiers et al. |
| 2003/0124028 | A1 | 7/2003 | Carlson et al. |
| 2003/0145647 | A1 | 8/2003 | Ismail et al. |
| 2003/0154031 | A1* | 8/2003 | Potyrailo et al. ............. 702/19 |
| 2003/0160194 | A1* | 8/2003 | Potyrailo et al. ...... 250/559.27 |
| 2003/0179002 | A1 | 9/2003 | Beylich et al. |
| 2003/0213292 | A1 | 11/2003 | Budeiri et al. |
| 2003/0222656 | A1 | 12/2003 | Phillips et al. |
| 2004/0231402 | A1 | 11/2004 | Eisenschmid et al. |

FOREIGN PATENT DOCUMENTS

| | | |
|---|---|---|
| DE | 10014724 A1 | 9/2001 |
| EP | 0102490 | 3/1984 |
| EP | 0 282 251 B1 | 3/1988 |
| EP | 0 282 251 B2 | 3/1988 |
| EP | 0282251 A2 | 3/1988 |
| EP | 0282251 | 9/1988 |
| EP | 0317356 B1 | 5/1989 |
| EP | 0676638 | 10/1995 |
| EP | 0769695 A2 | 4/1997 |
| EP | 0779510 | 6/1997 |
| EP | 0813236 | 12/1997 |
| GB | 1385488 | 8/1971 |
| GB | 2114745 | 8/1983 |
| GB | 2187286 | 9/1987 |
| JP | 59126931 | 7/1984 |
| JP | 60-134617 | 7/1985 |
| JP | 402161323 A | 6/1990 |
| JP | 05-129874 | 5/1993 |
| JP | 089112613 | 5/1996 |
| JP | 11094726 | 9/1997 |
| WO | WO91/02975 | 3/1991 |
| WO | WO95/13278 | 5/1995 |
| WO | WO98/01739 | 6/1997 |
| WO | WO98/15501 | 4/1998 |
| WO | WO98/37412 | 8/1998 |
| WO | WO99/18431 | 4/1999 |
| WO | WO99/51980 | 10/1999 |
| WO | WO 00/58709 | 3/2000 |
| WO | WO 00/67086 | 11/2000 |
| WO | WO 01/77624 | 10/2001 |
| WO | WO 02/12265 | 2/2002 |
| WO | WO 02/16888 | 2/2002 |
| WO | WO 02/23134 | 3/2002 |
| WO | WO 02/077613 | 10/2002 |
| WO | WO 03/014732 | 2/2003 |
| WO | WO 03/054482 | 7/2003 |
| WO | WO 03/100390 | 12/2003 |
| WO | WO 2004/036191 | 4/2004 |

OTHER PUBLICATIONS

"Cantilever Sensor Research Tool for Science and Industry", diScentris, Veeco.
Benes et al., "Viscosity Sensor Based on a Symmetric Dual Quartz Thickness Shear Resonator", pp. 1-7. 2003.
NSF Award Abstract #0239151, Feb. 6, 2003, pp. 1-2.
Nussbaum, "An Accurate Non-Radioactive Fluid Density Sensor", presentation to the Society of Petroleum Engineers, Bergen, Norway, Apr. 1, 2003.
Fleming, The Vibrating Tuning Fork Fluid Density Tool, pp. H1-H15.
"The Lubri-Sensor Electronic Oil Quality Analyser", www.pmlubricants.com, accessed on Feb. 5, 2004.
"Sensor Technology Improves Jet Engine Reliability", www.afrlhorizons.com, accessed on Feb. 5, 2004.
"Oil Quality Sensor", www.sae.org, accessed on Feb. 5, 2004.
Matsiev et al., "Application of Flexural Mechanical Resonators to Simultaneous Measurements of Liquid Density and Viscosity", 1999 IEEE UltraSonics Symposium, pp. 457-460.
"Refrigerant Flow in Evaporators", www.heatcrafteom.com, accessed on Feb. 5, 2004.
"Theory of the Vibrating Tuning Fork Fluid Density Tool", www.lancs.ac.uk, p. 1, accessed on May 7, 2003.
"A Vibrating Tuning Fork Fluid Density Tool", www. smithinst.ac.uk, p. 1, accessed on Feb. 2, 2004.
"SINIMS Oil and Gas Workshop", Draft: Notes of presentations and discussions, ICMS, Edinburgh, Mar. 11, 2002.
"Field Trials of The Viscosity & Fluid Density Tool (VFD)", Nan Gall Technology, published Aug. 2002.
"ViscoMaster HFO Viscosity Transmitter for Marine and Power Applications", Solartron Mobrey.
"CJV-5000 Vibro Viscometer Utilizing Tuning-Fork Technology", Yahoo Search accessed on Jun. 18, 2003.
"SOS-Smart Oil Sensor", Impact Technologies, LLC.
Pamphlet by Kavlico-A Solectron Company, Capability Brochure Industrial Sensors and Transducers.
A&D Weighing, SV Series Users' Handbook V1.04E, pp. 1-40.
"EPSON presents the MC-30A: Reliable 32.768kHz Dedicated to Automotive Applications", Aug. 25, 2003, www.epson.com, accessed on Feb. 11, 2004.
Lee et al., "A Remote Acoustic Engine Oil Quality Sensor", 1997 IEEE UltraSonics Symposium, pp. 419-422.
Zhang et al, "Contributions of Amplitude Measurement in QCM Sensors", IEEE Transactions on Ultrasonics, Ferroelectrics, and Frequency Control, vol. 43, No. 5, Sep. 1996, pp. 942-947.
Brand et al., Micromachined Viscosity Senso for Real-Time Polymerization Monitoring, 1997.
Chen et al., Resonance Response of Scanning Force Microscopy Cantilever, 1994.
Cleland and Rouke, Fabrication of High Frequency Nanometer Scale Mechanical Resonators from Bulk Si Crystals, Oct. 28, 1996.
Delphi, Intellik Oil Condition Sensor, 2002.
Dring and Jones, Integrated On-Line Multi-Sensing of Fluid Flow using a Mechanical Resonator, 2000.
Endo et al., Online Monitoring of the Viscosity in Dextran, 1990.
Ferry, John D., Viscoelastic Properties of Polymers, Jun. 2, 2005.
Fraunhofer, Sensors, 2001.
Grate et al., Smart Sensor System for Trace Organophosphorus and Organosulfur Vapor Detection Employing a Temperature-Controlled Array of Surface Acoustic Wave Sensors, Automated Sample Preconcentration, and Pattern Recognition, 1993.
Greenwood et al., Measurement of Viscosity and Shear Wave Velocity of a Liquid or Slurry for On-Line Process Control, Apr. 17, 2002.
Greenwood et al., On-Line Sensor for Density and Viscosity Measurements of a Liquid or Slurry for Process Control in the Food Industry, 1999.
Hammond et al., An Acoustic Automotive Engine Oil Quality Sensor.
Hammond et al., "Sensor".

Hauptmann et al., Ultrasonic Sensors for Process Monitoring and Chemical Analysis: State of the Art and Trends, Jun. 2005.
Hoenk et al., Surface Acoustic Wave Hygrometer: Measuring Water Vapor in Earth's Atmosphere, Mar. 16, 2002.
Jakoby et al., Viscosity Sensing using a Love-Wave Device, 1998.
Karrai, Lecture Notes on Shear and Friction Force Detection with Quartz Tuning Forks, Mar. 2000.
Landau et al., Fluid Mechanics, 1959.
Li et al., Electromechanical Behavior of PZT-Brass Unimorphs, 1999.
Lin et al., Operation of an Ultrasensitive 30-MHz Quartz Crystal Microbalance in Liquids, 1993.
Manalis et al., Two-Dimensional Micromechanical Bimorph Arrays for Detection of Thermal Radiation, Jun. 16, 1997.
Martin et al., Viscosity and Density Sensing with Ultrasonic Plate Waves, 1990.
Mason et al., Measurement of the Viscosity and Shear Elasticity of Liquids by Means of a Torsionally Vibrating Crystal, Jan. 29, 2004.
Merhaut, Josef, Theory of Electroacoustics, 1981.
Muramatsu et al., Viscosity Monitoring with Piezoelectric Quartz Crystal and its Application to Date, 1988.
Oden et al., Viscous Drag Measurements Utilizing Microfabricated Cantilevers, Jun. 24, 1996.
Polla et al., Processing and Characterization of Piezoelectric Materials and Integration into Microelectomechanical Systems.
Pujari et al., Reliable Ceramics for Advanced Heat Engines, Apr. 1995.
Sader, John E., Frequency Response of Cantilever Beams Immersed in Viscous Fluids with Applications to the Atomic Force Microscope, Mar. 30, 1998.
Shih, Wan, Simultaneous Liquid Viscosity and Density Determination with Piezoelectric Unimorph Cantilevers, Jan. 15, 2001.
Smith et al., Water Sorption Isotherms and Enthalpies of Water Sorption by Lysozyme using the Quartz Crystal Microbalance/Heat Conduction Calorimeter, Oct. 4, 2001.
Sorab et al., Engine Oil Viscosity Sensors Using Disks of PZT Ceramic as Electromechanical Vibrators, May 1997.
Technology.jpl.nasa, Surface Acoustic Wave Hygrometer, Mar. 16, 2002.
Troiler, Susan, Preparation of Chemically etched Piezoelectric Resonators for Density Meters and Viscometers, 1987.
Ulbrict, Helmar, Crimpen-eine Ausgereifte Anschlusstechnik.
Valimaki et al, Evaluation of an Equivalent Circuit Model for Thickness-Shear Mode Resonators in Liquids, Sep. 1996.
Wullner et al., Multi-Function Microsensor for Oil Condition Monitoring Systems.
Zhang et al., Determination of Liquid Density with a Low Frequency Mechanical Sensor Based on Quartz Tuning Fork, 2002.
Zeisel, Dieter, A Precise and Robust Quartz Sensor Based on Tuning Fork Technology for (SF6)—Gas Density Control, Oct. 12, 1999.
International Search Report PCT/US03/12503, Dec. 4, 2003.
International Search Report PCT/US03/32982, Oct. 17, 2003.
International Search Report PCT/US03/32983, Oct. 17, 2003.
International Search Report PCT/US2004/008531, Jun. 24, 2004.
International Search Report PCT/US2004/008552, Mar. 19, 2004.
Fisch M.R., et al., "Improved Acoustic Viscosimeter Technique", J. Acoust. Soc. Am., pp. 623, v. 60, No. 3, Sep. 1976.
Hlavay, J. and G.G. Guilbault, "Applications of the Piezoelectric Crystal Detector in Analytical Chemistry", Analytical Chemistry, pp. 1890-1898, v 49 No. 13, Nov. 1977.
Kanazawa, K. Keiji and Joseph G. Gordon II, "The Oscillation Frequency of a Quartz Resonator in Contact with a Liquid", Analytica Chimica Acta, pp. 99-105, Elsevier Science Publishers B.V. Amsterdam, 1985.
Kipling, Arlin L and Michael Thompson, "Network Analysis Method Applied to Liquid-Phase Acoustic Wave Sensors", Anal. Chem., pp. 1514-1519, 62, 1990.
Michels, A. et al., "1 MHz Quartz Length Extension Resonator as a Probe for Scanning Near-Field Acoustic Microscopy", Thin Solid Films, pp. 172-175, 264, 1995.
Muramatsu, Hiroshi et al., "Computation of Equivalent Circuit Parameters of Quartz Crystals in Contact with Liquids and Study of Liquid Properties", Anal. Chem., pp. 2142-2146, 60, 1988.

Muramatsu, H. et al., "A Quartz Crystal Viscosity Sensor for Monitoring Coagulation Reaction and Its Application to a Multichannel Coagulation Detector", Biosensors & Bioelelectronics, pp. 353-358, 6, Elsevier Science Publishers Ltd. England, 1991.
Nomura, T. and M. Iijima, "Electronic Determination of Nanomolar Concentrations of Silver in Solution with a Piezoelectronic Quartz Crystal", Analytica Chimica Acta, pp. 97-102, 131, Elsevier Scientific Publishing Company, 1981.
PCT International Search Report Form PCT/US97/18192, Apr. 27, 1998.
Newsam, J. et al., High Throughout Experimentation for the Synthesis of New Crystalline Microporous Solids, Microporous and Mesoporous Materials 48 355-365, 2001.
Akporiaye, D. et al., "Combinatorial Chemistry—The Emperor's New Clothes?." Microporous and Mosoporous Materials 48 pp. 367-373, 2001.
U.S. Appl. No. 09/420,334 entitled "Graphic Design of Combinatorial Material Libraries" (Lacy,.et al.), Oct. 18, 1999.
U.S. Appl. No. 09/305,830 titled "Synthesizing Combinatorial Libraries of Materials" (Rust, et al.), May 5,1999.
U.S. Appl. No. 09/755,623 entitled "Laboratory Database System and Methods For Combinatorial Materials Research"(Dorset, Jr. et al), Jan. 5, 2001.
The Family of Applications for U.S. Appl. No. 09/174,856 titled "Graphic Design of Combinatorial Material Libraries" (Lacy, et al.), Oct. 19, 1998.
U.S. Appl. No. 09/550,549 entitled "Automated Process Control and Data Management System and Methods" (Crevier, et al.), Apr. 14, 2000.
U.S. Appl. No. 09/800,819 entitled "Method and Apparatus for Characterizing Materials by Using a Mechanical Resonator", Mar. 7, 2001.
U.S. Appl. No. 09/580,024 entitled "Instrument for High Throughput Measurement of Material Physical Propertied and Method of Using the Same", May 26, 2000.
U.S. Appl. No. 10/155,207 entitled "High Throughput Microbalance and Methods of Using Same", May 24, 2002.
U.S. Appl. No. 09/285,963 entitled "Rapid Characterization of Polymers" (Safir et al), Apr. 2, 1999.
PCT International Search Report Form PCT/US02/17780, Oct. 21, 2002.
Nesbitt W. Hagood IV et al.., "Development of Micro-Hydraulic Transducer Technology", 10th International Conference on Adaptive Structures and Technologies, Oct. 11-13, 1999, Paris, France.
Pamphlet, "Hygroscopicity Measurement Apparatus," PUUMAN, no date.
Laine, E., and M. Aarnio, "Device for the Investigation of Humidy-related Behaviours of Materials," Department of Physics, University of Turku, no date.
Surface Acoustic Wave Hygrometer, http://technology.jpl.nasa.gov, accessed Mar. 16, 2002, 2 pages.
Hoenk, Michael, et al.., "Surface Acoustic Wave Hygrometer: Measuring Water Vapor in Earth's Atmosphere," http://mishkin.jpl.nasa.gov, accessed Mar. 16, 2002, 7 pages.
Trolier, Susan et al., "Preparation of Chemically Etched Piezoelectric Resonators for Density Meters and Viscometers", Mat. Res. Bull., vol. 22, pp. 1287-1274 (1987).
J.M. Hammond, R.M. Lee, D.G. Libby, XJ Zhang and L.A. Prager, "An Acoustic Automotive Engine Oil Quality Sensor", Transducers 97, S. 1343-1346.
H. Valimaki, J. Lekkala, H. Helle, "Evaluation of Equivalent Circuit Model for Thickness-Shear Mode Resonators in Liquids", Eurosensors X, Leuven, Belgium Sep. 11, 1996, S1377-1380.
H. Endo, K. Soda, I. Karube, H. Muramatsu, "Online Monitoring of the Viscosity in Dextran Fermentation Using Piezoelectric Quartz Crystal", Biotechnology and Bioengineering, vol. 36, S 636-641 (1990).
Mason W. P., Hill M., "Measurement of the Viscosity and Shear Elasticity of Liquids by Means of a Torsionally Vibrating Crystal", Transactions of A.S.M.E., 69 (1947) 359-370.
Barnes C., "An in vitro urea sensor using a torsion-wave crystal device", Sensors and Actuators B, 8 (1992) 143-149.

Schmitt N. et al., "A new method based on acoustic impedance measurements for quartz immunosensors", Sensors and Actuators B43 (1997) 217-233.

E. Bohmer, "Elemente der angewandten Elektrotechnik", Vieweg, Braunschweig, 1992 ( with English translation).

R.M. Langdon, "Vibratory Process Control Transducers".

H. Muramatsu, "Viscosity Monitoring with a Piezoelectric Quartz Crystal and Its Application to Determination of Endotoxin by Gelation of Limulus Amebocyte Lysate", Mar. 1988, Japan.

* cited by examiner

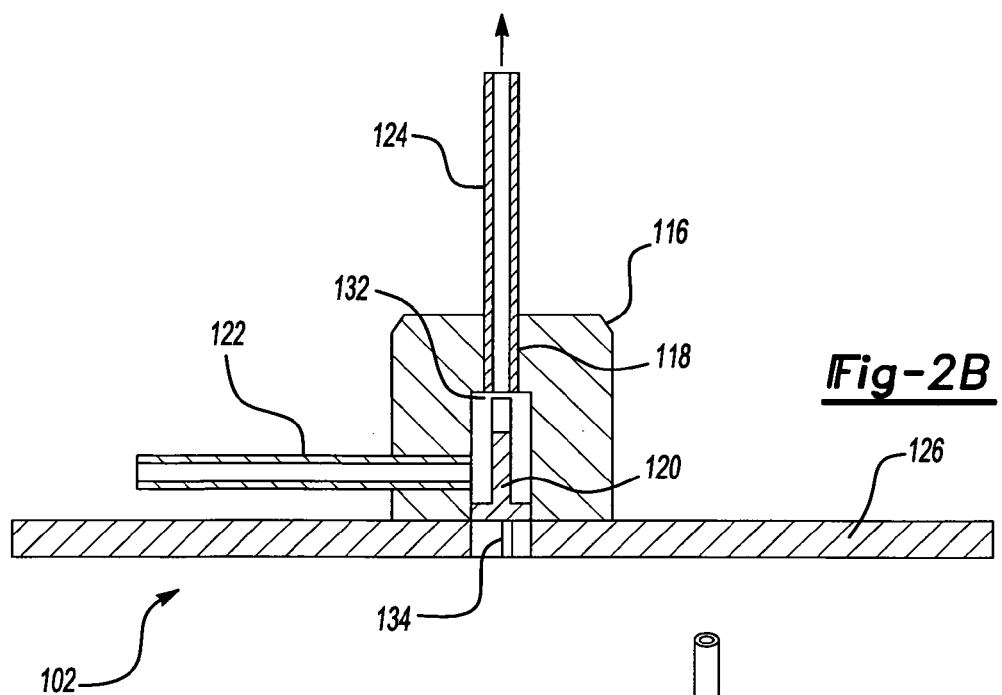
*Fig-2B*
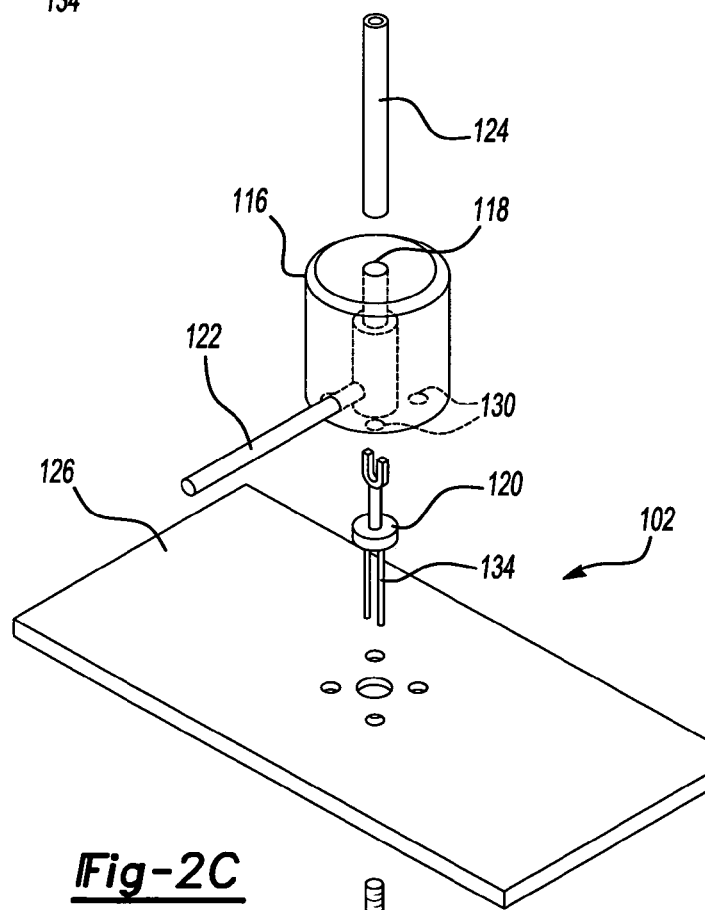
*Fig-2C*
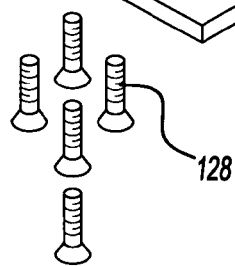

FLOW DETECTORS HAVING MECHANICAL OSCILLATORS, AND USE THEREOF IN FLOW CHARACTERIZATION SYSTEMS

CLAIM OF PRIORITY

The present application claims the benefit of the filing date of U.S. Provisional Application No. 60/296,638, filed Jun. 6, 2001 (entitled "Flow Detectors Having Mechanical Oscillators, and Use Thereof in Flow Characterization Systems Such As High Performance Liquid Chromatography and Flow-Injection Analysis Systems"), the contents of which are hereby expressly incorporated by reference herein.

TECHNICAL FIELD

The present invention generally relates to flow detectors suitable for applications in flow characterization systems such as high performance chromatography and flow-injection analysis systems. The invention relates, more specifically, to flow detectors effective for determining the viscosity, dielectric constant, conductivity and/or density of a fluid sample, from which other properties of the sample, such as molecular weight or concentration, can be derived. The invention particularly relates, in preferred embodiments, to flow detectors comprising one or more mechanical resonators or oscillators.

BACKGROUND OF INVENTION

Flow characterization systems, such as high performance liquid chromatography systems, gas chromatography systems, and flow-injection analysis systems, are well known in the art. Typically, in a liquid chromatography or a gas chromatography system, a sample is injected into a mobile phase (e.g., a liquid mobile phase or a gaseous mobile phase) being continuously supplied through a chromatography column and a flow detector. One or more sample components are chromatographically separated from each other in the chromatography column, and one or more properties of the separated components are detected in the flow detector. In a typical flow-injection analysis system, a sample is injected into a mobile phase being continuously supplied through a flow detector—directly, without substantial chromatographic separation thereof—and one or more properties of the samples or of components thereof are detected in the flow detector.

Parallel and rapid-serial analysis using high performance liquid chromatography or flow-injection analysis systems are likewise known, and have been applied to screen combinatorial libraries of samples. See, for example, WO 99/51980 and U.S. Pat. Nos. 6,260,407 to Petro et al, and 6,175,409 to Nielsen et al. Numerous types of flow detectors have been developed for application with liquid chromatography and/or flow-injection analysis systems, including for example, optical detectors such as refractive-index detectors, ultraviolet-visual detectors, photodiode array detectors, static-light-scattering detectors, dynamic-light-scattering detectors, and evaporative-light-scattering detectors (also known as evaporative mass detectors), and other types of detectors, such as capillary viscometer detectors, infrared detectors, fluorescence detectors, electrochemical detectors and conductivity detectors. In general, each of these detectors have advantages and disadvantages associated therewith, including for example with respect to sensitivity, universality and robustness. Moreover, most of the known detection systems are not well suited for application beyond traditional flow-characterization platforms. As such, there remains a need in the art for improved flow detectors, including flow detectors having improved sensitivity, universality and robustness, and preferably capable of being applied in connection with new emerging flow-characterization platforms, such as highly parallel liquid chromatography or flow-injection analysis systems. Parallel and serial analysis of samples using gas chromatography systems are also known in the art.

It has been suggested to employ a surface acoustic wave device in combination with a chromatograph in U.S. Pat. No. 5,533,402.

Mechanical oscillators or mechanical resonators, are known in the art as well. Recently, such oscillators have been applied to screen combinatorial libraries of fluid samples (e.g., liquid polymer samples) for various properties of interest, such as viscosity. See U.S. Pat. No. 6,182,499 to McFarland et al.

All patents and printed publications cited herein are hereby incorporated by reference for all purposes.

SUMMARY OF INVENTION

It is therefore an object of the present invention to provide flow detectors, and flow-characterization systems comprising such flow detectors, that allow for meaningful, rapid analysis of fluid samples.

Briefly, therefore, the present invention is directed to systems and methods for chromatographic analysis of samples, including liquid chromatography and gas chromatography systems and methods. The systems and methods include both single-sample chromatography systems and methods (such as for processing samples on a consecutive or serial format), as well as parallel systems and methods for simultaneously chromatographic analysis of samples. Generally, a chromatography system for characterizing a sample comprises a chromatography column including a stationary-phase within a separation cavity, a mobile phase source in fluid communication with the chromatography column for providing a mobile phase thereto, an injection valve for injecting samples into the mobile phase, and at least one flow detector in fluid communication with the chromatography column for detecting a property of the sample or a component thereof. One preferred flow detector of the present invention comprises one or more mechanical resonators in one or more detection cavities or cells. Such resonator flow detector is adapted to allow the sample-containing-mobile phase to contact the one or more resonators during a detection period. In operation, a fluid sample is injected into a mobile phase of a chromatography system, at least one sample component of the fluid sample is chromatographically separated from other sample components thereof, and a property of the fluid sample or of a component thereof is detected with a flow detector comprising a mechanical resonator.

The invention is also directed to flow-injection analysis systems and methods for analysis of samples. The systems and methods include both single-sample flow-injection systems and methods, as well as parallel systems and methods for simultaneously flow-injection analysis of samples. Generally, a flow-injection analysis system for characterizing a sample comprises a flow conduit—optionally in fluid communication with a flow column. The flow conduit and optional flow column each have an essential absence of chromatographic separation media, but can effect any such separation of sample components through non-chromatographic mechanisms, such as through differences in diffusion between sample components, filtration or another suitable technique. The system also includes a mobile phase source in fluid communication with the flow conduit and optional flow column, for providing a mobile phase thereto, an injection valve for injecting samples into the mobile phase, and at least one flow detector in fluid communication with the flow conduit and optional flow column, for detecting a property of the sample or a component thereof. One preferred flow detector, according to the present invention, comprises one or more mechanical resonators in one or more detection cavities. Such resonator flow detector is adapted to allow the sample-containing mobile phase to contact the one or more resonators during a detection period. In operation, a fluid sample is injected into a mobile phase of a flow-injection analysis system, the injected fluid sample is advanced to a flow detector without substantial chromatographic separation thereof, and a property of the fluid sample or of a component thereof is detected with the flow detector comprising the mechanical resonator.

The flow detector, for both chromatography systems and flow-injection analysis systems, and in either case, for both single-channel and parallel embodiments, can comprise, in addition to the one or more mechanical resonators, one or more circuits coupled with the one or more resonators. The one or more circuits can comprise a signal generator (e.g., a variable frequency signal generator capable of generating a variable frequency input signal, a constant frequency signal generator capable of generating an input signal having substantially the same frequency over time, or a combination thereof) for generating an input signal at one or more frequencies to oscillate the resonator during a detection period in which the sample or component thereof is in flowing contact with the resonator. The one or more circuits can also comprise a receiver for measuring the frequency response of the resonator during the detection period, such that a property of the sample or a component thereof can be determined from the measured frequency response. The receiver and the signal generator may be part of a single instrument or the functions may be split among plural separate instruments. In operation, the mobile phase comprising the sample or a component thereof is allowed to flow past the mechanical resonator, such that the sample or a component thereof contacts the resonator during a detection period. An input signal at one or more input frequencies is applied to a circuit coupled with the resonator to oscillate the resonator during the detection period, and the frequency response of the resonator is measured during the detection period. A property of the sample or a component thereof is then determined from the measured frequency response.

The flow detectors of the present invention, independently, and especially as applied in connection with chromatographic analysis systems and/or flow-injection analysis systems, offer advantages over known flow detectors. Specifically, the response of such resonator flow detectors to differences in, or to changes in, the physical and/or electrical properties of samples is unique as compared to the response of other types of detectors commonly used in chromatographic and/or flow-injection analyses. As such, the uniqueness of the resonator flow detectors can be translated into improved performance capabilities, including for example the performance of viscosity measurement—both in absolute values, and/or in comparative values, especially in connection with flow rate fluctuations during the analysis. As another example, resonator flow detectors can be applied as a concentration detectors that are substantially universal (as to the type of sample being analyzed), with sensitivities comparable to or better than known universal concentration detectors (e.g. such as refractive index detectors or evaporative light scattering detectors), and with improved response linearity. As a further exemplary advantage, both molecular weight and concentration information may be obtainable without a separate, independent concentration detector. Finally, the relative small size, and capability for close-in packaging offer unique opportunities for applications in parallel analysis systems, and in particular, in parallel microanalytical systems (e.g., microelectromechanical systems (MEMS)).

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 2A-2C are different views of a flow detector in accordance with the teachings of the present invention.

FIGS.

FIGS. 9A-9C are additional illustrative traces for comparison that are obtainable in accordance with the present invention.

DETAILED DESCRIPTION OF THE INVENTION

Figure 1:
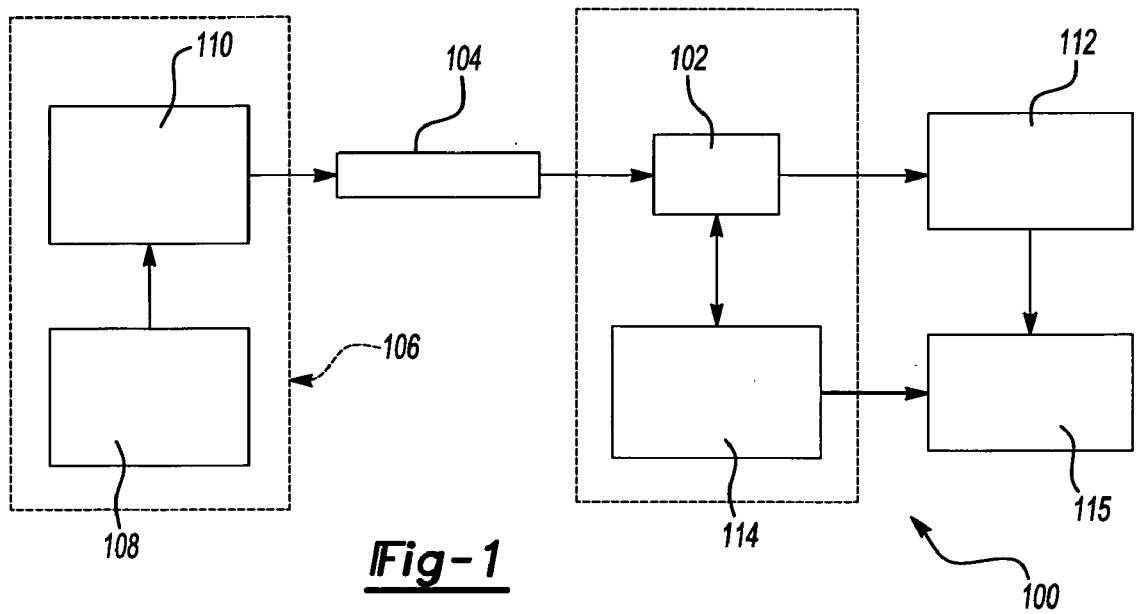
FIG. 1 is a schematic of one preferred system of the present invention.

In general, the present invention contemplates methods, devices and systems for determining a characteristic of a sample of a material, and preferably in a rapid, high-throughput manner. Thus, in one preferred embodiment, the methods of the present invention are premised upon a workflow that includes steps of (A) preparing the sample for analysis (which may further include a suitable dilution), (B) injecting the sample into a mobile phase of a flow characterization system (e.g., a chromatography system or a flow-injection analysis system), (C) optionally separating the sample chromatographically, (D) detecting a property of the sample or of a component thereof, and/or (E) correlating the detected property to a characterizing property of interest. Various characterization protocols may be employed involving some or all of the aforementioned steps. For example, a property of a sample may be detected in a non-flow, static system either with preparation (steps A and D) or without preparation (step D). Alternatively, a property of a sample may be detected in a flow characterization system—either with or without sample preparation and either with or without chromatographic separation. In characterization protocols involving flow characterization systems without chromatographic separation, a property of a sample may be detected in a flow-injection analysis system either with preparation (steps A, B and D) or without preparation (steps B and D). If chromatographic separation of a sample is desired, a property of the sample may be detected in a chromatography system either with preparation (steps A, B, C and D) or without preparation (steps B, C and D). While the detected property from samples being screened can be compared and ranked relative to each other on the basis of their performance, they could also be analyzed for absolute values (e.g., using a reference or calibration standard).

As will be discussed, though other independent uses are possible, the devices and systems of the present invention may be employed in connection with performance of the above workflow. In this regard, the devices and systems of the present invention are predicated upon the combination of a flow injection analysis instrument or chromatographic analysis instrument with a detector comprising a mechanical resonator, more particularly a mechanical resonator that is operated at a frequency of less than about 1 MHz, more preferably up to about 500 kHz, and even still more preferably up to about 250 kHz; for example, it is operated from about 1 to about 500 kHz, and more preferably in the range of about 5 to about 250 kHz, and still more preferably in the range of about 10 to about 100 kHz (e.g., about 28 to about 32 kHz). Further details of a preferred construction are described herein, together with illustrative examples.

In accordance with one aspect of the present invention, there is provided a method for characterizing a fluid sample, the method comprising the steps of injecting a fluid sample (e.g., liquid, gas or otherwise) into a mobile phase of a chromatography system (e.g., liquid, gas or otherwise), chromatographically separating at least one sample component of the fluid sample from other sample components thereof, and detecting a property of the fluid sample or of a component thereof with a flow detector comprising a mechanical resonator, with the preferred mechanical resonator including a torsional resonator, a flexural resonator or a combination thereof, such as a tuning fork resonator, and wherein the resonator is preferably operated at a frequency of less than about 1 MHz, more preferably up to about 500 kHz, and even still more preferably up to about 250 kHz; for example, it is operated from about 1 to about 500 kHz, and more preferably in the range of about 5 to about 250 kHz, and still more preferably in the range of about 10 to about 100 kHz (e.g., about 28 to about 32 kHz). Of course, it will be appreciated that other resonators may also be employed, such as alone, and more preferably in combination with a preferred torsional or flexural resonator, such as thickness shear mode resonator.

Another preferred method for characterizing a fluid sample, comprises the steps of injecting a fluid sample into a mobile phase of a flow-injection analysis system, advancing the injected fluid sample to a flow detector without substantial chromatographic separation thereof, and detecting a property of the fluid sample or of a component thereof with the flow detector, with the flow detector comprising an above described preferred mechanical resonator, operated at the above frequencies.

In one aspect of the present invention, either or both of the above methods, the property of the fluid sample or a component thereof is detected by a method that comprises allowing the mobile phase comprising the sample or a component thereof to flow past the mechanical resonator, such that the sample or a component thereof contacts the resonator during a detection period, applying an input signal at one or more input frequencies to a circuit coupled with the resonator to oscillate the resonator during the detection period, measuring the frequency response of the resonator during the detection period, and determining a property of the sample or a component thereof from the measured frequency response.

The input signal may be applied at a substantially constant frequency during the detection period, or at two or more frequencies during the detection period. Further, the property of the sample or component thereof may be determined from the measured frequency response by comparison to a calibration curve showing the measured frequency response at that input frequency for two or more known samples. The input signal may also comprise a variable frequency input signal, and thus the method further comprises varying the frequency of the input signal over a predetermined frequency range during the detection period, such that a frequency-dependent response of the resonator can be measured. Preferably, the predetermined frequency range is determined by a method that comprises determining the resonance frequency of the mechanical resonator while the resonator is in flow contact with the mobile phase.

In addition, when the input signal is a variable frequency input signal, the method might further comprise varying the frequency of the input signal over a predetermined frequency range for a first frequency scan during a first portion of the detection period, such that a frequency-dependent response of the resonator can be measured during the first portion of the detection period, varying the frequency of the input signal over the predetermined frequency range for a second frequency scan during a second portion of the detection period, such that a frequency-dependent response of the resonator can be measured during the second portion of the detection period, varying the frequency of the input signal over the predetermined frequency range for a third frequency scan during a third portion of the detection period, such that a frequency-dependent response of the resonator can be measured during the third portion of the detection period, and determining a property of the sample or a component thereof from the measured frequency response during each of the first, second and third portions of the detection period.

It may also be possible to vary the frequency of the input signal over the predetermined frequency range for one or more additional frequency scans during one or more additional portions of the detection period, such that a frequency-dependent response of the resonator can be measured during the one or more additional portions of the detection period. Frequency scan rate may be the same or vary. For example, for the above, the first, second and third frequency scans may be effected at an overall average frequency scan rate of not less than about one, or possibly even three or more, five or more, or even ten or more frequency scans per second. For example it may be possible to achieve this by suitably controlling the size of the injected sample and the mobile phase flow rate. In this regard, it will also be appreciated that the composition of any mobile phase may vary or remain substantially constant over time. Further, the frequency of the input signal over time may be varied to compensate for any such variation in mobile-phase composition.

As will be discussed further herein, the flow detector of the present invention may comprise two or more mechanical resonators, which may be the same or different relative to each other. It is thus possible that the mobile phase can be allowed to flow past each of the two or more resonators such that the sample or component thereof contacts each of the two or more resonators during the detection period. The input signal for each of the two or more resonators may be applied at a common, constant frequency during the detection period, or at different, constant frequencies during the detection period.

In one aspect, the input signal for one or more of the two or more resonators is a variable frequency input signal, and a preferred method further comprises varying the frequencies of the input signals over a common predetermined frequency range, over different predetermined frequency ranges during the detection period, or a combination thereof, such that a frequency-dependent response can be measured for each of the two or more resonators during the detection period.

In one particularly preferred construction, the preferred flow detector of the present invention comprises a mechanical resonator placed in a fluid passageway (e.g., for defining a detection cavity), an inlet for providing fluid communication between the detection cavity and a mobile phase source, and an outlet for providing fluid communication between the detection cavity and a mobile phase sink. One highly preferred structure orients the inlet and the outlet substantially orthogonal to each other, though the inlet and outlet may also be in substantial linear alignment with each other.

The present invention can be employed with a flow characterization instrument (e.g., a chromatograph or flow injection analyzer) that is operated using art-disclosed serial (e.g., consecutive sequence) or parallel (e.g., simulataneous) techniques, such as for sample injection, sample separations, input signal generation, signal monitoring, or other property detection of two or more samples, using one or more detectors. Thus it is possible that the properties of first and second or additional fluid samples or components thereof are detected substantially simultaneously or sequentially in one or more flow detectors, such as by measuring the frequency responses of any resonators substantially simultaneously or sequentially during the detection period.

The structure of any flow characterization system employed herein is not critical. However, it is preferred that a chromatography instrument include a column comprising a separation cavity, an inlet port for receiving a mobile phase and for supplying a sample to the separation cavity, an effluent port for discharging the mobile phase and the sample or separated components thereof from the separation cavity, and a stationary-phase within the separation cavity, a mobile phase source in fluid communication with the inlet port of the chromatographic column for providing a mobile phase thereto, an injection valve adapted to provide for selective fluid communication with the mobile phase for injecting samples into the mobile phase, and a resonator flow detector in fluid communication with the effluent port of the chromatographic column for detecting a property of the sample or a component thereof.

A suitable flow injection analysis instrument preferably includes a flow conduit, optionally in fluid communication with a flow column, the flow conduit and optional flow column each having an essential absence of chromatographic separation media, a mobile phase source in fluid communication with the flow conduit and optional flow column, for providing a mobile phase thereto, an injection valve adapted to provide for selective fluid communication with the mobile phase for injecting samples into the mobile phase, and a resonator flow detector in fluid communication with the flow conduit and optional flow column, for detecting a property of the sample or a component thereof.

A suitable flow injection analysis instrument preferably includes a flow conduit, optionally in fluid communication with a flow column, the flow conduit and optional flow column each having an essential absence of chromatographic separation media, a mobile phase source in fluid communication with the flow conduit and optional flow column, for providing a mobile phase thereto, an injection valve adapted to provide for selective fluid communication with the mobile phase for injecting samples into the mobile phase, and a resonator flow detector in fluid communication with the flow conduit and optional flow column, for detecting a property of the sample or a component thereof.

One illustrative system of the present invention includes a flow characterization apparatus, a resonator detector and data acquisition hardware. As seen from FIGS. 1 and 2, a preferred system 100 of the present invention includes a resonator flow detector 102 adapted to be placed in fluid communication with the sample (or components thereof) either upstream of, downstream of, or both, any chromatography column, flow injector, or effluent port. By way of illustration, the embodiment of FIG. 1 illustrates placement of the resonator detector in a system in which an optional, suitable separation component 104 (e.g., an elongated chromatography column such as one having approximate dimensions of about 30 cm ×7 mm, or available under the designation PL-Gel Mixed-B from Polymer Laboratories) has been inserted between a flow system 106 (e.g., including a pump 108, an auto-sampler 110, or one or more additional or alternative components) and the flow detector 102. An optional evaporative light scattering detector (ELSD) or other optional suitable detector 112 (e.g., operated at about 100° C. with about 1.5 L/min of air flowing through) is connected directly or indirectly to an outlet of the flow detector 102.

The flow detector 102 is also preferably coupled with suitable hardware 114 for generating, receiving or a combination thereof, a signal for any resonator housed in the flow detector 102. For example, a lock-in amplifier (e.g., of a type such as an SR830 (or possibly an SR 810 or 850) DSP Lock-In Amplifier from Stanford Research Systems) may be coupled with a resonator for assisting in monitoring resonator response to a change of condition within the detector. Any of a number of suitable hardware devices may be employed, as the skilled artisan with appreciate, particularly with reference to commonly-owned patent properties, including, for example, the subject matter shown in U.S. Pat. Nos. 6,336,353 (Matsiev, et al.)("Method and apparatus for characterizing materials by using a mechanical resonator"); and 6,182,499 (McFarland, et al.) ("Systems and methods for characterization of materials and combinatorial libraries with mechanical oscillators"); and U.S. patent application Ser. Nos. 09/723,818, 09/800,819, and 09/133,171, hereby expressly incorporated by reference for all purposes. The teachings of U.S. patent application Ser. No. 10/155,207 ("High Throughput Microbalance and Methods of Using Same") may also be adapted herein, and the same is hereby expressly incorporated by reference for all purposes.

Preferably, one or both of the resonator flow detector 102, and any other detector 112 that might optionally be employed, are in direct or indirect signaling communication with a suitable processor 115, such as a personal computer, and preferably one that includes software that functions for one or a combination of setting-up instrument parameters, controlling instrument parameters, running analyses, generate results, storing results, organizing results, or publishing data reports (e.g., a PC employing MILLENIUM™ data management software, such as is commercially available from Waters Corporation of Milford, Mass.).

One particularly preferred construction for a flow detector of the present invention includes an inlet portion, a detection portion (such as, for example, including a flow passageway in which the resonator is at least partially located), and an outlet portion. Preferably the inlet portion is adapted for fluid communication with the flow characterization system (e.g., downstream from the separation component), and the outlet portion is adapted for fluid communication with any additionally serially configured detector, a waste collection system, or the like. Optionally, the flow detector includes a suitable housing or frame for enclosing or otherwise holding any electrical components or other hardware associated with the detector.

Figure 2A:
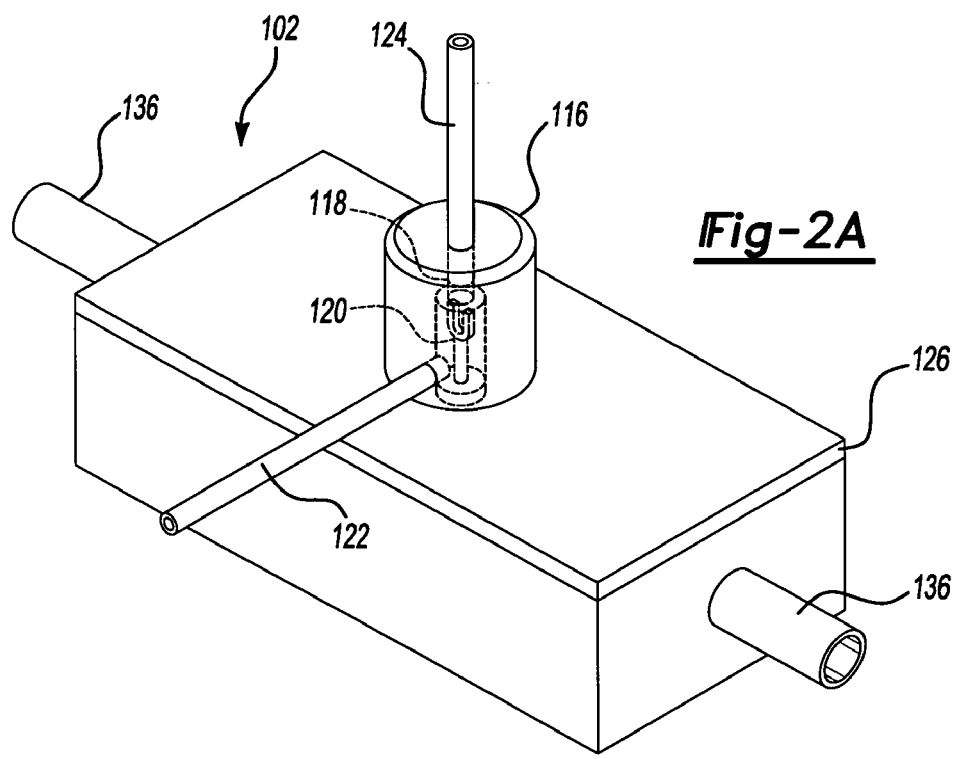

Turning in more detail to FIGS. 2A-2C, one illustrative resonator flow detector 102 is shown. The detector 102 includes a detector head 116 having a passageway 118 defined therein for providing a sample flow path. The passageway is adapted for receiving and holding a resonator 120 in sensing relation to any sample that passes through the passageway. In this regard, the detector will include at least one or a combination of a suitable inlet conduit (e.g. inlet capillary) 122, or a suitable outlet conduit (e.g. outlet capillary) 124. A housing 126 is optionally provided, which can be assembled together with the head 116, such as by the use of fasteners 128 that are received in apertures 130. Of course, such structure may be varied, such as by integrating the fasteners to the head. Further, the housing function might be performed by suitable structure fabricated in the detector head itself (e.g., combining the head with the housing), so as to reduce the number of overall components. It will be appreciated that even though one preferred approach is to arrange the inlet and outlet conduits generally orthogonally relative to each other, other orientations are also possible, such as directly in line with each other, parallel to each other, at an acute angle relative to each other, at an obtuse angle relative to each other, forming one or more curves relative to each other or otherwise.

It will be appreciated that there will preferably be a detection cell 132, defined between the inlet conduit and outlet conduit in the head 116, with suitable volume for conducting measurements in accordance with the teachings herein. The detection cell 132 may be any suitable size or shape and preferably it has an internal volume of about 1 to about 500 microliters and more preferably about 5 to about 50 microliters, e.g. about 15 microliters. The detection cell 132 may include some or all of the passageway 118. It is possible that the entirety of the passageway defines the detection cell 132.

One or a plurality of leads 134 associated with the resonator 120 preferably are connected to the signaling hardware of the present invention. For example, one preferred approach is for any lead 134 to penetrate a wall of the housing and then connect with suitable cables. This may be done in any suitable manner. By way of example, in one embodiment, one or more connectors, such as a bayonet nut connector (BNC) 136, are attached to the housing 126, for affording ease of connection with additional hardware.

In accordance with the above, data is acquired using the lock-in amplifier, preferably in combination with a suitable network analyzer. For example, a network analyzer can be used to identify the frequency of resonance of one or more resonators of the present flow detector, as well as to find a frequency that is most sensitive to the changes in the viscosity of eluent. Thus, by way of illustration, an analog signal is generated by the lock-in amplifier, which is preferably tuned to a frequency below about 1 MHz, more preferably below about 500 kHz, and even still more preferably below about 250 kHz; for example, it is tuned to a frequency of from about 1 to about 500 kHz, and more preferably in the range of about 5 to about 250 kHz, and still more preferably in the range of about 10 to about 100 kHz (e.g., to a frequency of about that of the resonator, e.g., about 28.10 kHz), and even more preferably slightly above or below (e.g., within about 50% of the frequency and more preferably within about 25% of the frequency of resonance of a preferred tuning fork resonator).

It is noted that an example of a preferred tuning for resonator is that available commercially from Citizen Corporation tuning fork, under part number CFS308-32.768KDZFB. Other tuning fork resonators may also be employed. For example, if a dead volume of the detector is desired to be smaller than about 5 uL, a tuning fork resonator available from ESC (Taiwan), part # ESC-.327-8-14 may be used.

It will be appreciated that, in general, a preferred tuning fork resonator herein will include two or more substantially elongated forks or tines joined at a first common end through a common member, each of the two or more forks having two primary surfaces in substantially parallel opposition to each other, two edge surfaces in substantially parallel opposition to each other, and a second free end surface substantially opposed to the first common end. Other structures, of course, are also possible. In practice of one embodiment of the present invention, the resonator may be orientated in the flow detector such that the direction of bulk mobile phase flow is substantially parallel to the primary surfaces of the forks. It is also possible that the direction of bulk mobile phase flow is substantially normal to the primary surfaces of the forks. Other intermediate angular orientations are also possible.

As explained throughout the specification, torsional or flexural resonator detectors, and especially tuning fork detectors are particularly preferred for use in the present invention for a number of reasons, including for instance that tuning fork detectors are suitable for construction with relatively smaller dead volumes, as compared with a typical viscometric detector (e.g., less than about 75 microliters, more preferably less than about 50 microliters, and still more preferably less than about 20 microliters, as compared with typical volumes of about 100 uL for the most efficient viscometric detectors believed to be presently commercially available). The tuning fork detectors are thus capable of and indeed produce relatively sharper peaks and higher resolution power as compared with such existing detectors. In addition, the preferred resonator detectors of the present invention will generally be operated under resonance conditions such that any acoustic wave generation from the resonator is substantially avoided for substantially the entirety of the volume of sample that is flowed over the resonator.

The resonator is placed in signaling communication with (e.g., connected with a short cable, or otherwise in electrical, magnetic, optical, thermal, or other communication) to an input of the lock-in amplifier, and more preferably to a high impedance input of the lock-in amplifier (e.g., of about 0.1 to about 5 megaOhm and about 1 to about 100 pF, and more preferably about 2 megaohm and 20 pF).

The lock-in amplifier is preferably operated in an output offset mode and with the expansion of the output at a magnitude on the order of at least about 10 times, and more preferably about 100 times. A suitable amplifier output channel (e.g., the "R" channel output of the amplifier), which is the amplitude of the detected signal is suitably connected (e.g., via a SAT/IN box coupled with a BusLace board) to the computer 115, preferably equipped with the data management software discussed previously.

It will be appreciated that the hardware of the present invention, in one aspect, is secured in a fixed location. It will be appreciated, however, that the components may be translatable relative to each other as well. It may also be possible to employ a suitable robot arm (e.g., such as that available from Tecan Systems (formerly Cavro Scientific Instruments) (San Jose, Calif.)) for translating the hardware components and sample relative to each other.

It will be appreciated from the above that viscosity, density, dielectric field or another property can be monitored directly or derived from a measurement, such as by calculation, from the flow detector in accordance with the above by any of a number of different approaches. For example, without limitation, it is possible to monitor the change in electrical feedback from the resonator while maintaining a constant driving amplitude or vibration amplitude (or combination thereof) at a predetermined frequency. The monitoring that occurs may be monitoring the change of frequency of the resonator while maintaining the input signal to the resonator as a constant. It may alternatively employ the monitoring of the change in electrical feedback from the resonator while maintaining a constant frequency. In a particularly preferred embodiment, the input signal is a variable frequency input signal and the monitoring includes varying the frequency of a variable frequency input signal over a predetermined frequency range to obtain a frequency-dependent resonator response of the mechanical resonator.

The measured response can then be correlated with viscosity, density, dielectric field or another property using art-disclosed methods. For instance, relative sample performance might be analyzed and compared with each other. Absolute measures might also be taken, such as by measuring responses and comparing them against responses obtained from know reference or calibration standards.

By way of illustration, in one embodiment of the present invention, absolute values are obtained for a particular property such as viscosity, molecular weight, concentration or a combination thereof. Though other approaches are possible, one preferred approach is to monitor the resonator detector response for one or a plurality of reference or calibration standards having known property values. The data can be correlated for corresponding a particular detector response with a known property. For example, a plot may be prepared against which later data obtained for samples of unknown property can be compared. This can be performed manually, with a computer, by plots, calculation or otherwise.

In another embodiment, it may be possible to employ the above steps in combination with additional steps using the data obtained as an input value from which another property, which is dependent upon the input value, can be derived, such as by calculation. For example, as illustrated further herein, upon determination of molecular weight, a suitable molecular weight dependent property such as viscosity can be calculated using an equation that correlates viscosity as a function of molecular weight, such as the Mark-Houwink Equation.

It is also possible that one or more properties may be derived from a second detector, which is adapted for the purpose of measuring and providing data about a property. For example, data might be obtained from a mass detector (e.g., an ELSD), and such data employed in combination with data obtained from the resonator flow detector of the present invention. Accordingly, the present invention contemplates performance of any or all of the above techniques.

It will be appreciated that measurements taken in accordance with the present invention may be taken continuously (e.g., as real-time), in spaced intervals, or a combination of both. To illustrate, for taking measurements at intervals, it is desirable to take at least one measurement prior to injection of a sample into the resonator detector. At least one measurement is taken while the sample is in the cell. Optionally, another measurement is taken after the sample leaves the cell.

The operation parameters of the system of the present invention are not critical. By way of illustration, in the embodiment described above, the mobile phase preferably is employed at a flow rate ranging from about 0.01 mL/min to about 100 mL, and more preferably about 0.1 to about 10 mL/min (e.g., about for a THF mobile phase, or the like, a flow rate of about 1 mL/min). It will be appreciated that other operational parameters can also be successfully employed using the teachings herein. For example, it may be attractive to employ a variable flow mode or stop flow mode, in accordance with art-disclosed teachings such as are found in U.S. Pat. No. 6,175,409, hereby incorporated by reference.

Though other flow characterization instruments may be employed, a particularly preferred flow characterization system is a chromatograph (e.g., comprise, for instance, one or a plurality of injection valves or injection loops, injection ports, chromatographic columns, or effluent ports) that is preferably suitably equipped with a pump, optional solvent degasser, and optional autosampler (e.g., a robotic autosampler having one or a plurality of robot arms, and optional heated probes). One or a plurality of detectors preferably are located upstream of the effluent port. Any suitable chromatograph device may be used, and the device may be adapted for HPLC, GPC or another form of chromatography. An example of one preferred commercially available device useful in the present invention is that available from Waters Corporation of Milford, Mass., under the name Alliance™ HPLC. A suitable detector may be an ELSD detector commercially available from Polymer Laboratories, such as the PL-ELS 1000 evaporative light scattering detector. It will be appreciated that other devices may also be employed.

Details of general and specific aspects of the flow characterization systems, and especially liquid chromatography systems and flow-injection analysis systems are provided in the following co-owned, related patents and patent applications, each of which is hereby incorporated by reference for all purposes: U.S. Pat. No. 6,175,409 to Nielsen et al. entitled "Flow Injection Analysis and Variable-Flow Light Scattering Apparatus and Methods for Characterizing Polymers"; Ser. No. 09/285,963, filed Apr. 2, 1999 by Safir et al., entitled "Rapid Characterization of Polymers"; Ser. No. 09/285,393 (now U.S. Pat. No. 6,265,226) entitled "Automated Sampling Methods for Rapid Characterization of Polymers", filed Apr. 2, 1999 by Petro et al.; Ser. No. 09/285,333 (now U.S. Pat. No. 6,260,407) entitled "High-Temperature Characterization of Polymers", filed Apr. 2, 1999 by Petro et al.; Ser. No. 09/285,392 (now U.S. Pat. No. 6,294,388), entitled "Indirect Calibration of Polymer Characterization Systems", filed Apr. 2, 1999 by Petro et al.; and Ser. No. 09/410,546 (now U.S. Pat. No. 6,296,771) entitled "Parallel High Performance Liquid Chromatography with Serial Injection", filed Oct. 1, 1999. Collectively, these patents and applications are referred to herein as the Flow Characterization Applications and Patents. In particular, the types of fluid samples, injection subsystems and approaches, chromatographic columns and approaches, and flow-injection analysis systems and approaches are each described in great detail in such Flow Characterization Applications and Patents.

In operation of one preferred chromatography instrument of the present invention, a mobile-phase fluid is pumped from a mobile-phase reservoir by a pump through the injection valve, chromatographic column and detector. The pump can be controlled with a microprocessor. The mobile phase can be exhausted from the system via effluent port into a waste collection container. A sample is loaded into an injection valve through an injection port, and the loaded sample is injected into the mobile phase of the chromatographic system. The injected sample is chromatographically separated in the chromatographic column. A property of the sample, one or more separated components thereof, or both, is then detected while the sample resides in the detector. A microprocessor (e.g., computer) is typically in electronic communication with the detector to collect, process and analyze the data obtained therefrom. While the same microprocessor can be used for the pump control and data acquisition, these functions could be effected with separate microprocessors.

The geometry of the separation columns employed herein may be selected as desired. In some preferred embodiments, conventional columns may be employed, such as those that are relatively long and narrow (e.g., ranging from about 4-8 mm in diameter and from about 30-50 cm in length, respectively). However, the use of shorter and wider columns is also possible. For example, it is possible to employ a column that has a diameter: height ratio of from about 0.3 to about 1, and can also range from about 0.5 to about 1. An example of a preferred commercially available column is a GPC column (30 cm×7 mm PL-Gel Mixed-B, available from Polymer Laboratories) Under any approach, one or a plurality of columns (e.g., three or four columns) may be employed in series for each separation.

The chromatographic column typically comprises a separation medium having a stationary-phase within a separation cavity, either with or without an inert support for the stationary phase. The column can also comprise one or more fillers, frits, fittings and or other desired features appropriate for its intended application. The particular separation medium to be employed as the stationary-phase is not critical. Typical stationary-phase media can be a bed of packed beads, rods or other shaped-particles, or a monolithic medium (typically greater than about 5 mm in thickness). Generally, a preferred stationary-phase includes a porous media, such as are suitable for gel permeation chromatography (GPC), or media suitable for precipitation-redissolution chromatography, adsorption chromatography, and/or reverse-phase chromatography. Non-porous particles or empty columns and/or capillaries with adsorptive walls can be used as well. If beads are employed, spherical beads are preferred. Examples of particularly preferred stationary-phase media may be selected from silica, cross-linked resins, hydroxylated polyglycidyl methacrylates,(e.g., poly(2-3-dihydroxypropylmethacrylate)), poly(hydroxyethyl methacrylate), polystyrenic polymers such as poly(styrene-divinylbenzene), or the like.

The mobile-phase fluid employed is also not generally critical, and can vary depending on the chemistry of the separation being effected. An exemplary mobile-phase fluid may include one or more of tetrahydrofuran (THF), toluene, dimethylformamide, water, aqueous buffers, trichlorobenzene and dichlorobenzene. Exemplary mobile-phase fluids for precipitation-redissolution chromatography include THF, methanol, hexane, acetone, acetonitrile and water. For adsorption chromatography, the mobile phase can include, for example, hexane, isooctane, decane, THF, dichloromethane, chloroform, diethylether, acetone or combinations thereof.

It will also be appreciated that even though disclosed herein in connection with the use of a chromatographic separation, the present invention can omit the separation operation or associated structure and simply provide a detector for a flow-characterization system that incorporates a flow-through detector without regard to the performance of a separation step. Further, a flow characterization system might employ a separation. For example, some analysis systems can include an apparatus for non-chromatographic separations (e.g., filtration). Moreover, a sample can be prepared, prior to analysis, by separating one or more components of the raw sample from other components thereof using any suitable art-disclosed technique.

It will be appreciated that any of a number of different modifications may be made to the structure and operation of the flow characterization systems of the present invention. For example, the flow characterization systems can include additional reservoirs, and additional pumps to provide more than one mobile-phase fluid, to provide a mobile-phase composition gradient or even to provide a mobile-phase phase temperature gradient. Further, it will be appreciated that the type of chromatography is not limited to the preferred embodiments shown, but that the flow detector devices of the present invention may be used in any of a number of different types of chromatography including, for example, one or a combination of art-disclosed precipitation-redissolution chromatography, size exclusion chromatography, liquid chromatography, adsorption chromatography, reverse-phase chromatography, or gel permeation chromatography techniques.

Additional guidance in the construction of a suitable flow characterization system can be gained from the above-noted Flow Characterization Applications and Patents, the teachings of all of which are hereby incorporated by reference. Thus, it will be recognized that a flow characterization system of the present invention may include one or more additional detectors, for use alone or in combination with the resonator flow detector of the present invention, such as a suitable flow-injection mass detector or other suitable detector (e.g., one or more of an evaporative light scatter detector, a dynamic light-scattering detector, a static light-scattering detector, an evaporative mass detector, a refractive index detector, capillary-viscometric detector, photodiode array detector, infra-red detector, fluorescence detector, electrochemical detector, conductivity detector, ultraviolet-visible absorbance detector or the like). The system may optionally be calibrated using calibration standards having known properties. "Universal" standard practices may be employed, as may "indirect calibration standards".

The employment of a flow detector according to the present invention is particularly advantageous for the purpose of monitoring viscosity of a sample that is passed through the flow characterization system. As will also be discussed herein, it also may be suitably employed for measuring concentration, molecular weight, dielectricity, density or other related properties.

Details of general and specific aspects of mechanical resonator or oscillator detection systems are described in the following co-owned, related patents and patent applications, each of which is hereby incorporated by reference for all purposes: U.S. Pat. No. 6,182,499 to McFarland et al. entitled "Systems and Methods for Characterization of Materials and Combinatorial Libraries with Mechanical Oscillators"; Ser. No. 09/723,818 entitled "Systems and Methods for Characterization of Materials and Combinatorial Libraries with Mechanical Oscillators" filed Nov. 28, 2000; Ser. No. 09/133,171 entitled "Method and Apparatus for Characterizing Materials by Using a Mechanical Resonator" filed Aug. 12, 1998; Ser. No. 09/801,165 entitled "Method and Apparatus for Characterizing Materials by Using a Mechanical Resonator" filed Mar. 7, 2001; and Ser. No. 09/800,819 entitled "Method and Apparatus for Characterizing Materials by Using a Mechanical Resonator" filed Mar. 7, 2001 (collectively referred to herein as Mechanical Oscillator Patents and Applications). The teachings of U.S. Pat. application Ser. No. 10/155,207 ("High Throughput Microbalance and Methods of Using Same") may also be adapted herein, and the same is hereby expressly incorporated by reference for all purposes. In particular, the types of resonators, and operation thereof for detecting various properties are described in the aforementioned Mechanical Oscillator Patents and Applications. The terms "resonator" and "oscillator", when used in the context of the detectors of the present invention, are employed interchangeably.

In one embodiment, a resonator flow detector in accordance with the present invention comprises a single mechanical resonator. It is also possible that a plurality of different resonators may be combined into a single detector, or a plurality of different resonators be separated into a plurality of detectors.

In one aspect of this embodiment, the input signal can be applied at a single, substantially constant frequency. The single, substantially constant frequency is preferably a predetermined frequency that is the resonance frequency for the mechanical resonator under the analysis conditions (e.g., in that mobile phase, at that flow-rate, with that type of sample, etc.). Where the input signal is applied as a single, substantially constant frequency, differences in measured response frequencies and/or changes in measured response frequencies can be used to provide meaningful information about the sample being analyzed—even if absolute values for the property are not determined. For example, a property of the sample or component thereof can be determined from a measured frequency response curve by comparing the measured frequency response to a calibration curve. The calibration curve can include values of the measured frequency response at that input frequency for known samples, for example, for known samples evaluated in the same mobile phase.

In another aspect of the embodiment having one or a plurality of mechanical resonators in the detector, the input signal can be applied at two or more different frequencies during the detection period. In one such preferred embodiment, though not required in all embodiments, the input signal is preferably a variable frequency input signal. The frequency of the input signal can be varied, preferably over a predetermined frequency range, during the detection period, such that a frequency-dependent response of the resonator can be measured. The predetermined frequency range can be a range of frequencies surrounding the resonance frequency of the mechanical resonator while the resonator is in flow contact with the mobile phase. The frequency range can vary, for example, as about ±20% of the resonance frequency, or preferably about ±10% of the resonance frequency. Advantageously, where the input signal is applied as a variable frequency, differences in measured response frequencies and/or changes in measured response frequencies can be used to provide meaningful information about the sample being analyzed, including absolute values for the property being determined. Additionally or alternatively, however, a property of the sample or component thereof can also be determined from a measured frequency response curve by comparing the measured frequency response to a calibration curve. The calibration curve can include values of the measured frequency responses over the range of input frequencies for known samples, for example, for known samples evaluated in the same mobile phase.

In a particular preferred approach, a single sample or sample component (e.g., single separated component of an HPLC system) can be evaluated by effecting multiple scans over the sample during the detection period, with each scan covering a range of frequencies. More specifically, the frequency of the input signal can be varied over a predetermined frequency range for a first frequency scan during a first portion of the detection period, such that a frequency-dependent response of the resonator can be measured during the first portion of the detection period. Thereafter, the frequency of the input signal can be varied over the predetermined frequency range for a second frequency scan during a second portion of the detection period, such that a frequency-dependent response of the resonator can be measured during the second portion of the detection period. Optionally thereafter, the frequency of the input signal can be varied over the predetermined frequency range for a third frequency scan during a third portion of the detection period, such that a frequency-dependent response of the resonator can be measured during the third portion of the detection period. In many cases, it will be desirable to vary the frequency of the input signal over the predetermined frequency range for one or more additional frequency scans during one or more additional portions of the detection period, such that a frequency-dependent response of the resonator can be measured during the one or more additional portions of the detection period. In any case, the property of the sample or a component thereof is determined from the measured frequency response during each of the first, second and third and/or additional portions of the detection period. The rate of scanning in this embodiment is not narrowly critical, but can be described as follows. Generally, the first, second and third frequency scans are effected at an overall average frequency scan rate of not less than about one frequency scan per second, at an overall average frequency scan rate of not less than about three frequency scans per second, and more preferably at an overall average frequency scan rate of not less than about ten frequency scans per second. In flow characterization systems of the invention, the size of the injected sample and the mobile phase flow rate can be controlled such that five or more frequency scans of the sample or components thereof are effected during the detection period, and preferably, such that ten or more frequency scans of the sample or components thereof are effected during the detection period.

It will be appreciated from the above that additional variations are also possible. For example, a first resonator flow detector may be employed in parallel or serially upstream or downstream of a second or additional resonator flow detector and the resonators therein operated at the same or a different frequency relative to each other. A first resonator flow detector may be employed upstream of a separation column and a second or further additional resonator flow detector employed downstream of the separation column, with the resonators therein operated at the same or a different frequency relative to each other.

The preferred resonators or oscillators for the detectors herein are intended to include mechanical piezoelectric resonators, and particularly quartz resonators. A highly preferred mechanical resonator for employment herein is a flexural resonator such as a tuning fork resonator, which offers an advantage of being able to be oscillated at a relatively low frequency range (e.g., in a preferred embodiment, it is operated in the range of less than about 1 MHz, more preferably up to about 500 kHz, still more preferably about 1 to about 100 kHz, (e.g., about 32 kHz)). Preferably, the resonators of the present invention are also selected so that they will not excite acoustic waves in a sample of sufficient magnitude that the measurements would be compromised.

As indicated, the present invention is not intended to be limited to tuning fork resonators. Other types of resonators can be used, such as thickness shear mode resonators, tridents, cantilevers, torsion bars, bimorphs, membrane resonators, length extension resonators, torsion resonators, unimorphs, or various surface acoustic wave devices, or combinations thereof. More preferred resonators are selected from tuning forks (e.g., two-tine, tridents or the like), cantilevers, bimorphs, or unimorphs. A plurality of the same type or different types of resonators of resonators can be used in combination. For example, a low frequency resonator may be employed with a high frequency resonator. In this manner, it may be possible to obtain a wider range of responses for a given sample.

It will be appreciated that a tuning fork herein is an excellent candidate for providing a detector for measuring small amounts of mass change in a flow characterization system. Without intending to be bound by theory, because the resonance frequency and the damping of the tuning fork resonator depends on the effective mass of a tine and the amount of "drag" of the tine in contact with a sample, any change in the mass on the tine mass or the amount of drag will change the resonance response of the tuning fork. An increase in the mass associated with the tuning fork will therefore reduce the resonance frequency of the tuning fork in a measurable way.

Any resonator used herein optionally may be coated with a material to change the performance characteristics of the resonator. For example, the material can be a coating, such as to protect the resonator from corrosion or other factors potentially affecting resonator performance. Alternatively, it may be a specialized "functionalization" coating that changes the resonator's response if a selected substance is present in the composition being tested by the resonator. For example, adding a hydrophobic or hydrophilic functionality to a tuning fork tine allows the tine to attract or repel selected substances in the medium being analyzed, changing the mass or effective mass of the tuning fork and thereby changing its resonance frequency.

The resonators can also be functionalized with a polymer layer or other selective absorbing layer to detect the presence of specific molecules in a vapor. The coating or functionality can be applied onto the resonator using any known method, such as spraying or dipping. Further, the specific material selected for the coating or functionality will depend on the specific application in which the tuning fork resonator is to be used. J. Hlavay and G. G. Guilbault described various coating and functionalization methods and materials to adapt piezoelectric crystal detectors for specific applications in "Applications of the Piezoelectric Crystal Detector in Analytical Chemistry," Analytical Chemistry, Vol. 49, No. 13, November 1977, p. 1890, incorporated herein by reference.

A single tuning fork resonator may be coated or functionalized. Alternatively, multiple resonators having the same or a different structure, the same or different coatings and/or the same or different functionalities can be incorporated into one sensor. For example, a plurality of tuning fork resonators may have the same structure but have different functionalities, each functionality designed to, for example, bond with a different target molecule. When the sensor is used in such an application, one tuning fork resonator can, for example, be functionalized with a material designed to bond with a first substance while another resonator can be functionalized with a material designed to bond with second substance. The presence of either one of these substances in the sample composition being tested will cause the corresponding tuning fork resonator to change its resonance frequency.

As discussed in the above, in other embodiments, the flow detector can comprise a detector that comprises two or more mechanical resonators. The mechanical resonators can be the same or different, with respect to design and/or performance, and in some embodiments, are preferably substantially the same. Similarly, the two or more resonators can be operated at one or more common, substantially constant input frequencies, or at two or more different, substantially constant input frequencies. Alternatively, one of the resonators can be operated at a single, substantially constant input frequency, while another of the two or more resonators are operated at two or more variable frequencies. As another alternative, both of the two or more resonators can be operated at variable input frequencies, over the same ranges or over different ranges of frequencies.

It should also be appreciated that even though the present invention is disclosed, in one preferred aspect, as a screening technique as part of a combinatorial research program (e.g., for a polymer research or production program in which extent of dissolution must be measured, the presence or absence of targets identified or otherwise), it has other applications, including but not limited to the provision of a detector for measuring quantities (e.g., relatively small quantities) in a commercial (rather than a research) environment, such as a real time or an on-line process monitoring, process control or other quality control measure in which a flow characterization system is employed. Examples of the various applications to which the present invention is particularly suited include, without limitation, detecting viscosity (e.g., intrinsic, relative, specific, or a combination thereof), molecular weight, molecular weight distribution, branching coefficient, or the like. Thus, methods of the present invention also contemplate the operation of the present systems in the latter mentioned applications. The present invention lends itself particularly well for bulk property measurements, such as may be necessary, for example, for monitoring polymer properties.

In a combinatorial approach for identifying or optimizing materials, properties, conditions or reactions, a large compositional space (e.g., of variable structures or ratios of components) or a large reaction condition space (e.g., of temperature, pressure, humidity or reaction time) may be rapidly explored by preparing libraries of 2 or more, 4 or more, 16 or more, 48 or more, or even 96 or more samples (e.g., using an art-disclosed techniques, such as is set forth in U.S. Pat. No. 5,776,359 (Schultz, et al)), and then rapidly screening such libraries. The libraries may be synthesized or screened on a common substrate or two or more different substrates. They may be synthesized or screened using art-disclosed rapid-serial, parallel, serial-parallel or hybrid parallel-serial approaches. The number of samples that can be analyzed as part of a combinatorial research program is not limited herein. By way of example, the number of samples can be 4 or more, 20 or more, 100 or more, 150 or more, 400 or more, 500 or more, 750 or more, 1,000 or more, 1,500 or more, 2,000 or more, 5,000 or more and 10,000 or more samples. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 5.

Another unique aspect of the combinatorial approach of the present invention is that it allows considerable flexibility in performing research and requires relatively small samples. Thus, even though the sample size is not narrowly critical, it can generally vary, depending on the particular characterization protocols and systems used to characterize the sample or components thereof. Typical sample sizes can range from about 0.1 microliter to about 1 ml, more typically from about 1 microliter to about 1000 microliters, even more typically from about 5 microliters to about 100 microliters, and still more typically from about 10 microliters to about 50 microliters. A generally preferred sample size for flow characterization systems and, particularly for liquid chromatography, is a sample size of about 20 microliters.

Samples within a library may differ, including with regard to chemical structure, processing or synthesis history, mixtures of interacting components, post-synthesis treatment, purity, etc. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial research applications, at least two or more, preferably at least four or more, even more preferably eight or more and, in many cases most, and allowably each of the plurality of samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In a particularly preferred embodiment, the samples are spatially separated, such that members of the library of samples are separately addressable. All samples in a library may be the same or different relative to each other. When process conditions are to be evaluated, for example, the libraries may contain only one type of sample. The use of reference standards, controls or calibration standards may also be performed, though it is not necessary. The samples of a library may be previously characterized, uncharacterized or a combination thereof, so that property information about the samples may not be known before screening.

Combinatorial approaches for screening a library can include an initial, primary screening, in which material samples are rapidly evaluated to provide valuable preliminary data and, optimally, to identify several "hits"—particular candidate samples having characteristics that meet or exceed certain predetermined metrics (e.g., performance characteristics, desirable properties, unexpected and/or unusual properties, etc.).

It may be advantageous to screen more focused libraries (e.g., libraries focused on a smaller range of compositional gradients, or libraries comprising compounds having incrementally different structural variations relative to those of the identified hits) and additionally or alternatively, subject the initial hits to variations in process conditions. Once one or more hits have been satisfactorily identified based on the primary screening, libraries focused around the primary-screen hits might be further evaluated with a secondary screen—a screen designed to provide (and typically verified, based on known materials, to provide) chemical composition, sample content or process conditions that relate with a greater degree of confidence to commercially-important important processes and conditions than those applied in the primary screen. Particular samples that surpass the predetermined metrics for the secondary screen may then be considered to be "leads." If desired, identified lead samples may be subsequently prepared in bulk scale or otherwise developed for commercial applications through traditional bench-scale and/or pilot scale experiments.

The present invention is not limited to the performance of a single characterization, but may include a plurality of different characterization steps relative to a sample of interest. For example, in one approach, two or more characterization systems can be used to screen each of a plurality of samples for two or more properties of interest—one property being determined by a first detector, another property being determined by a second or additional detector. In an alternative approach, a first characterization system can be used to prescreen each of a plurality of samples for a first property of interest, and then a second characterization system can be used to rescreen certain selected samples—for the same or for a different property of interest—with the selection for the second screen being based on results from the first pre-screening. Briefly, four or more samples are screened to determine a first property of interest in a first screen. A figure of merit is determined for the four or more samples. The figure of merit is preferably based, at least in part, on the first determined property of interest. The determined figure of merit for the four or more samples is compared with a predetermined threshold value for the figure of merit. The threshold value can be based, for example, on results with a then-best-known system. Those samples of the four or more samples that favorably compare with the predetermined threshold value for the figure of merit are then screened with the second characterization system. In a preferred embodiment, only those samples that favorably compare to the predetermined figure of merit are screened with the second characterization system.

Accordingly, from the discussion herein it is possible that a resonator detector is used alone (e.g., in a flow characterization instrument with or without chromatographic separation) or in combination with one or more serially-configured, parallel-configured other detectors such as one or more of an evaporative. light scatter detector, a dynamic light-scattering detector, a static light-scattering detector, an evaporative mass detector, a refractive index detector, capillary-viscometric detector, photodiode array detector, infrared detector, fluorescence detector, electrochemical detector, conductivity detector, ultraviolet-visible absorbance detector or the like.

As will be appreciated from the above, the present invention may also be employed by itself or in combination with other screening protocols for sample analysis. For example, it is contemplated that the present invention involves measuring a first characteristic of a sample in combination with at least one or a plurality of additional other characterization steps, such as X-ray analysis, chromatography, mass spectrometry, optical screening, infrared screening, electrochemical screening, mechanical property screening, or the like. Without limitation, examples of other screening techniques, which might be combined with the analysis of the present invention, include those addressed in commonly-owned U.S. Pat. Nos. 6,371,640 (Hajduk, et al); 6,182,499 (McFarland, et al); 6,175,409 B1 (Nielsen, et al); 6,157,449 (Hajduk, et al); 6,151,123 (Nielsen); 6,034,775 (McFarland, et al); 5,959,297 (Weinberg, et al), 5,776,359 (Schultz, et al.), commonly owned and co-pending U.S. patent application Ser. No. 09/580,024 titled "Instrument for High Throughput Measurement of Material Physical Properties and Method of Using Same," filed on May 26, 2000, all of which are hereby expressly incorporated by reference herein.

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more polymer samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

The average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently identify a polymer sample or component thereof having a particularly desired property (e.g., such as weight-average molecular weight). In short, the search can be accelerated for the particular property of research interest.

Preferably the system of the present invention is automated and makes use of a computer or other microprocessor for one or more aspects of its operation. Thus, one or more microprocessors can, as noted above, be employed for controlling every aspect of the flow characterization systems, including any pump (e.g., mobile-phase flow-rate, flow-rate gradients, compositional gradients, temperature gradients, acceleration rates for such gradients); reservoir (e.g., temperature, level); auto-sampler (e.g., movements between spatial position, timing thereof, sample selection, sample preparation, sampling pump flow-rates, and other operations); injection valve (e.g., timing, selection of sample loops, etc.); column (e.g., column selection (if multiple columns and automated column-switching valves are present), column temperature); detector (e.g., data acquisition (e.g., sampling rate), data processing (e.g., correlation); the detector parameters (e.g., wavelength); and/or for controlling overall system conditions (e.g., system pressure, temperature). Suitable operational software is typically available from detector or chromatography system manufacturers (e.g., MILLENIUM™ 2000 software available from Waters Corporation of Milford, Mass.).

In a preferred embodiment, the system of the present invention may also be driven by suitable software for designing a library, controlling the instruments for mechanical property screening, and data acquisition, viewing and searching, such as LIBRARY STUDIO®, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.); or a combination thereof. The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. patent application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands for controlling activity at such individual address.

As mentioned throughout this description, it is common in the practice of the present invention that a sample is synthesized upon or is transferred to a substrate from which it is analyzed using the system of the present invention. Substrates as employed herein may be in any suitable form and preferably will have a rigid or semi-rigid surface on which or into which one or an array of samples can be formed or deposited. The substrate can be of any suitable material, and preferably consists essentially of materials that are inert with respect to the samples of interest. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques.

As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In preferred embodiments, the substrate is designed such that the individually addressable regions of the substrate can act as reaction vessels for preparing a reaction product (possibly as well as sample containers for the two or more different samples during subsequent characterization thereof). Unlined or lined (e.g., glass-lined) 96-well, 384-well and 1536-well microtiter-type plates, fabricated from stainless steel, aluminum, plastic or the like are also preferred substrates for a library of samples. The choice of an appropriate specific substrate material and/or form for certain applications will be apparent to those of skill in the art in view of the guidance provided herein.

As gleaned from this description, the present invention finds utility in a number of applications, and is especially useful as employed in a combinatorial polymer science research program, and/or for quality monitoring or control for industrial polymer synthesis or processing protocols. The invention is not limited to use for polymer analysis. For example, some aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal oxides or other ceramic compounds, metal salts, metal colloids, metal ligands, etc., without particular limitation.

Many variations of the present invention will be appreciated by the skilled artisan. Without limitation, for example, the present invention may also be employed in a flow characterization analysis pursuant to which the effective separation time is reduced by serially overlapping samples, and thus processing a given sample is being closer in time to any preceding sample, successive sample or both, thereby enhancing overall sample-throughput. More specifically, and in accordance with the teachings of U.S. Pat. No. 6,260,407 (Petro et al), hereby incorporated by reference, a plurality of polymer samples can be characterized by injecting a first polymer sample into a mobile phase of a liquid chromatography system, separating at least one sample component of the injected first sample from other sample components thereof in a chromatographic column, and detecting at least one property of the separated sample component of the first sample. The second polymer sample is then injected into the mobile phase of the liquid chromatography system at a particularly-controlled time, referred to for purposes herein as the successive-sample injection time. At least one sample component of the injected second sample is separated from other sample components thereof, and at least one property of the separated sample component of the second sample is detected. The cycle is repeated for each pair of preceding/successive samples in the plurality of samples. In preferred applications, at least 8 different samples are characterized according to the method.

Separations performed hereunder are not limited strictly to the above discussed techniques, and others may be employed. For example, non-chromatographic separation optionally can be effected with one or more in-line filters.

The composition of the mobile phase can be substantially constant over time, or can vary over time—e.g., such as in composition gradient elution chromatography. Where the composition of the mobile phase varies over time, the frequency of the input signal can also be varied over time to compensate for the variation in mobile-phase composition on detector response. Similary, the temperature of the mobile phase can be substantially constant over time, or can vary over time. Where the temperature of the mobile phase varies over time, the frequency of the input signal can be varied over time to compensate for the variation in mobile-phase temperature on detector response.

In another high-temperature characterization protocol, a sample can be characterized in a liquid chromatographic system that employs a compositional gradient to the mobile phase for selectively eluting one or more components of sample from the chromatographic column. In yet another polymer characterization protocol, a polymer sample can be characterized in a liquid chromatographic system that employs a temperature gradient to the mobile phase for selectively eluting one or more components of polymer sample from the chromatographic column.

Any of a number of different sample preparation steps may also be employed. For example, typical sample preparation steps include preliminary, non-chromatographic separation of one or more components of a polymer sample from other components, dilution, mixing and/or redissolution (e.g., from a solid state), among other operations.

Though a preferred application of the flow detectors of the present invention is to measure viscosity, in another preferred embodiment the flow detector of the present invention is employed as a universal concentration detector, particularly by use of conductivity, viscosity, density or even dielectric sensitivity measurements. More specifically, the flow detectors of the present invention are capable of sensing molecules carried (e.g., dissolved) in eluent by comparison of measurements for the carried sample versus measurements or known values for the pure eluent (or eluent otherwise absent the sample). The detectors of the present invention are especially sensitive to any changes in dielectric characteristics of an environment, particularly those caused by a difference in polarity of detected molecules and molecules of eluent.

In one particular aspect of this embodiment, a series of tuning forks, either in a single cell or in a series of separate cells, permits for distinguishing changes in dielectric characteristics over a desired time interval (e.g., as a result of changes in mobile phase composition during gradient HPLC elution) from faster changes caused, for instance, by a zone of analyte passing through the cell. That further enhances the ability to use the flow detector of the present invention as a universal detector, especially for gradient elution HPLC. By way of example, one preferred system might employ a plurality of tuning forks (e.g., three tuning forks), arranged serially, with and intermediate tuning fork that is adapted to sense changes relative to the tuning fork that precedes and succeeds it. Thus, the system is capable of normalizing the signal for a continuous drift of the mobile phase properties.

In light of the detailed description of the invention and the examples presented above, it can be appreciated that the several objects of the invention are achieved, including but not limited to the ability through the use of the present flow detector to sense viscosity at performance level comparable to or better than commercially available viscometric detectors; to detect sample (e.g., polymer sample) concentration levels approximating that of commercially available high sensitivity ELSD detectors; to improve sensitivity to flow rate fluctuations relative to typical viscometric detectors based on capillary bridges; to provide improved linearity relative to existing ELSD detectors; to offer a wider dynamic range and sensitivities relative to typical commercially available refractive index detectors; the ability to be packaged separately from other electronics and hardware in view of its compact size; the agility offered by quick response calibration; or others. The flow detector also offers the ability to serve as a universal concentration detector of sensitivity comparable or higher than that of existing universal or group selective concentration detectors (refractive index detectors, ELSD), and possibly for use in gradient HPLC. Further, it might be possible to obtain both molecular weight and concentration information from the flow detector without another concentration detection, as required in any other case of molecular weight-sensitive detection.

The following examples further illustrate the principles and advantages of the invention. In these examples, a flow detector is employed in accordance with the teachings of the present invention, and specifically one employing a tuning fork resonator, such as the detector shown in FIGS. 1A-1C. Similar results are believed possible and within the scope of the present invention for other types of resonators that are substituted for or used in combination with a tuning fork resonator, such as other mechanical flexural or torsional resonators. Further, though illustrated in connection with certain samples of a particular chemistry, other samples may be analyzed with similar types of results (albeit quantitatively different) are possible in accordance with the present invention. Thus, the methodologies presented are not intended to cover only the specific materials mentioned, but cover the more generic use of the methodologies. By way of example, the illustrated use of polystyrene standards could be substituted with a standard of another plastic or other material. Moreover, the representative output that is depicted in the accompanying Figures is not intended to be limited to the specific examples illustrated, though again it is possible and likely that different quantitative results will occur depending upon the different samples employed.

EXAMPLE 1

Figure 3:
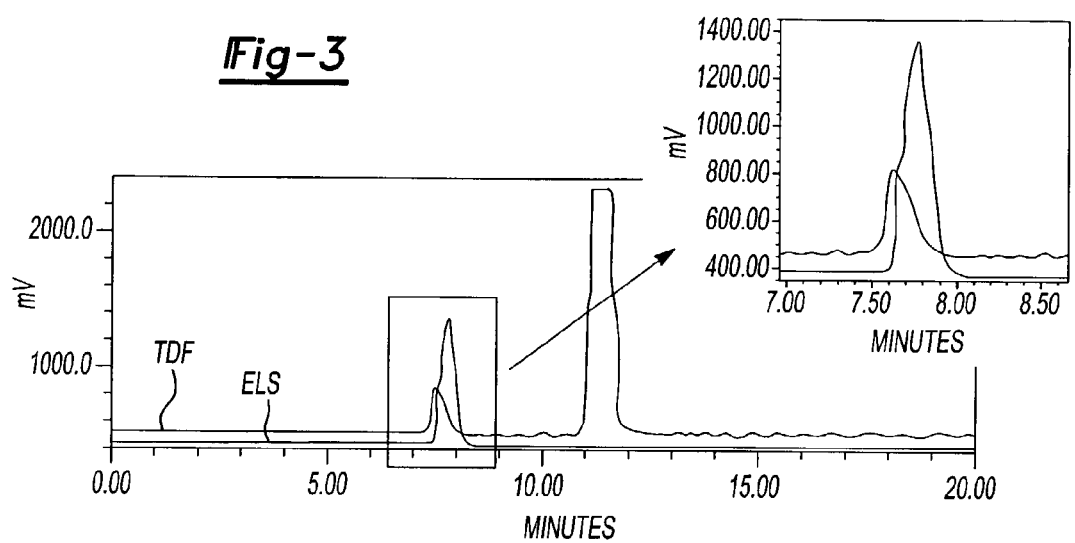
FIG. 3 is a plot of signal versus time for use for detection of a sample after an illustrative chromatographic separation.

Referring to FIG. 3, there is shown a plot of signal versus time for use of the present flow detector for detection of a polydisperse polymer after chromatographic (e.g., GPC) separation. After quick optimization of signal generation and data acquisition conditions, a sample (e.g., about 5 µL of polystyrene solution (molecular weight of approximately 200k at concentration of approximately 5 mg/mL in toluene)) is injected. The sample of solution is passed through a flow detector of the present invention (e.g., employing a tuning fork resonator (TFD)). The sample is also passed through a downstream ELSD. The chromatographic traces from both TFD and ELSD detectors are compared in FIG. 3. It can be seen that the sensitivity of TFD is satisfactory for chromatographic analysis. In contrast to ELSD, TFD is sensitive also to small molecules via differences in dielectricity. Toluene, in which the polystyrene sample has been dissolved gives a large peak (cut off by data acquisition board) at a retention time of about 11.5 minutes.

EXAMPLE 2

Figure 4A:
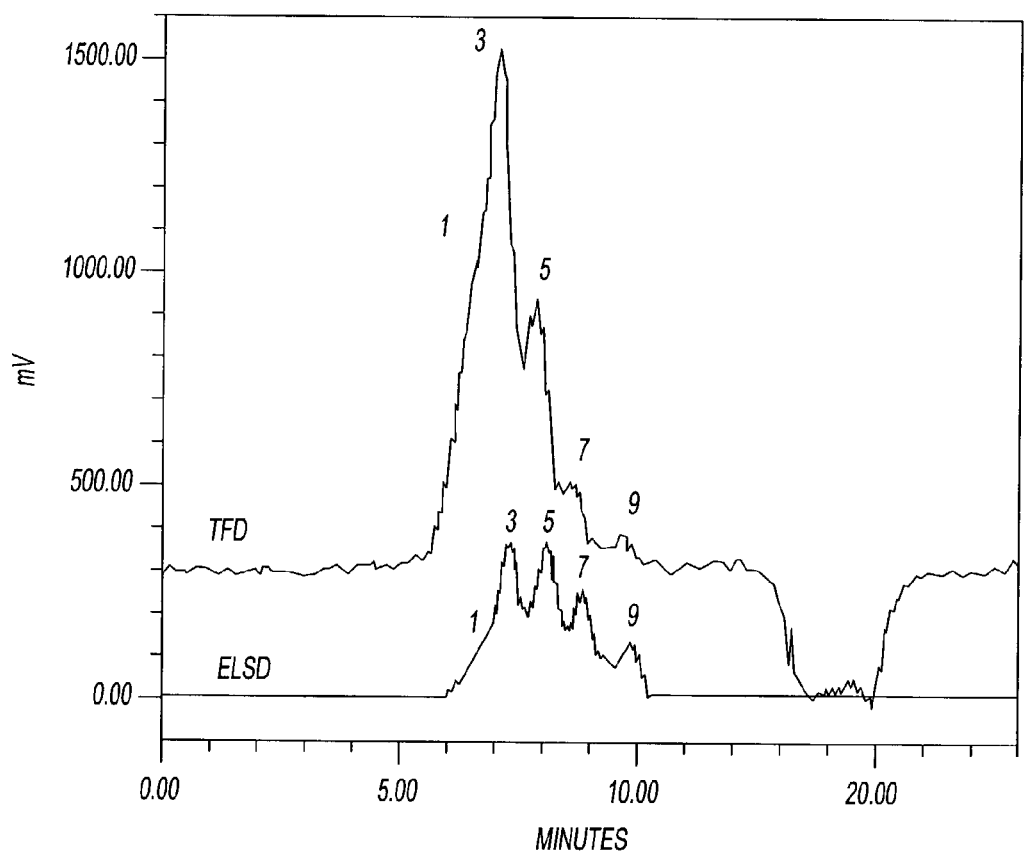
FIGS. 4A and 4B are plots of signal versus time obtainable in use of the present flow detector for monitoring the separation of a sample mixture.
Figure 4B:
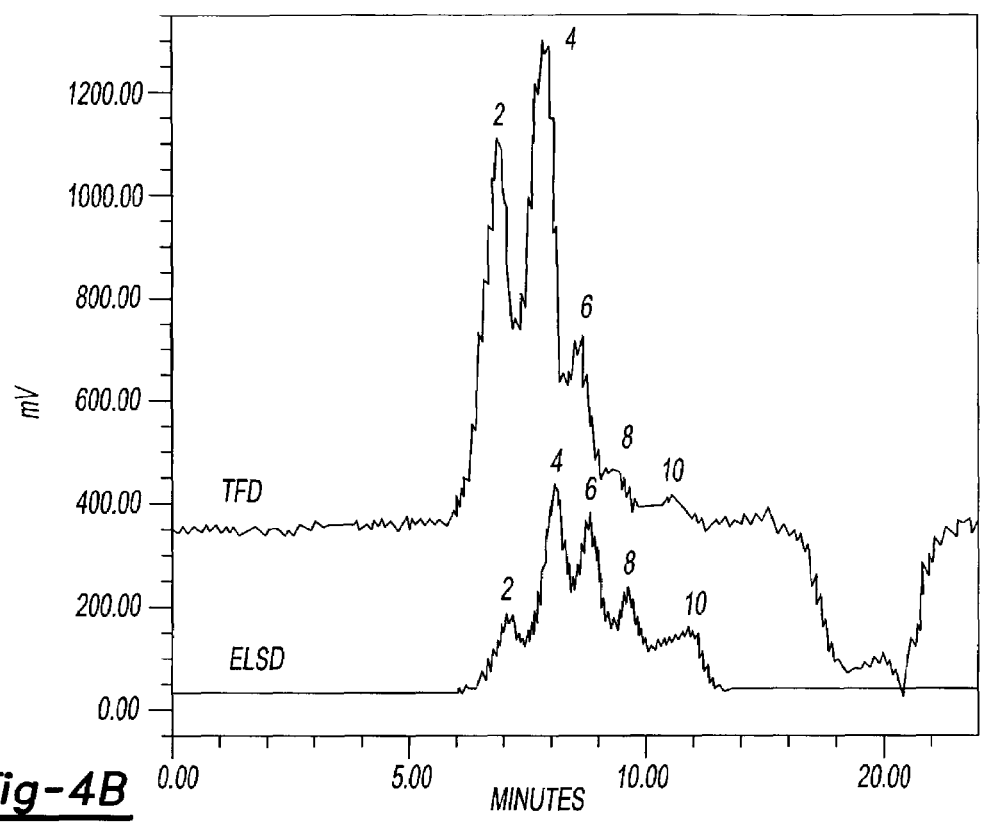
Figure 5A:
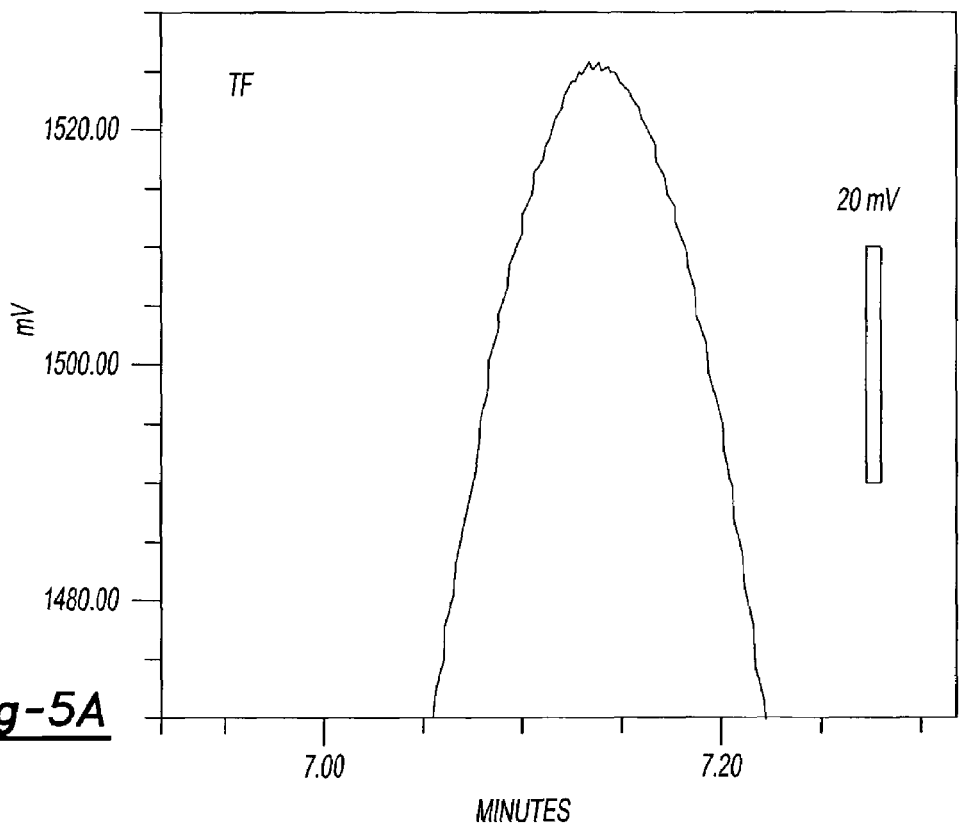
FIGS. 5A and 5B correspond to top regions of the peak 3 in the chromatogram of FIG. 4A.
Figure 5B:
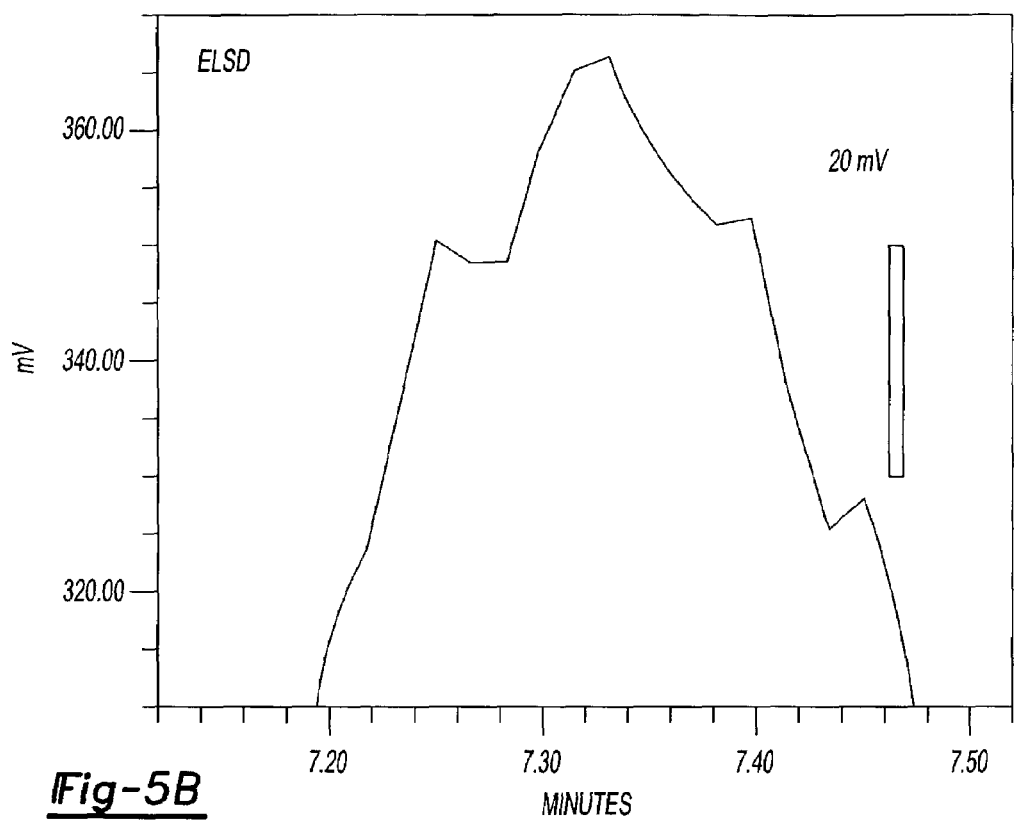

Referring to FIGS. 4A and 4B, there is shown a plot of signal versus time in use of the present flow detector for monitoring the separation of a sample (e.g., polymer sample) mixture. In this example, two mixtures (corresponding respectively to that depicted in FIGS. 4A and 4B) of narrow polystyrene standards of different molecular weights (1—7.5M, 2—2.5M, 3—840k, 4—320k, 5—150k, 6—60k, 7—30k, 8—11k, 9—3k, 10—580) are injected into a system as in Example 1 in order to compare responses of TFD and ELSD detectors as a function of molecular weight. Although ELSD corresponds to concentration, TFD response is molecular weight sensitive. Therefore, it is expected that viscosity contributes significantly to the TFD response, in addition to dielectricity and density changes of environment in the detector. The zoomed-in portions of the chromatograms shown in FIGS. 5A and 5B correspond to top of the peak 3 in the chromatogram of FIG. 4A, for both the TFD and ELSD data respectively.

It is also seen that even if TFD gives approximately +/− 1 mV signal fluctuation on a baseline with asperities of frequency of about one per 10 second, the smoothness of traces during the signal changes is better than that of ELSD. The TFD signal fluctuations, which make the TFD signal look more noisy than that of ELSD, can probably be suppressed by stabilization of the temperature around the flow detector and more perfect equilibration of the system (washing out any trace impurities). It is believed that the electronic noise of TFD signal is about two orders of magnitude lower than the signal asperities mentioned above, primarily because of steps generated by amplifier's signal digitalization, and about the same as electronic noise of ELSD (0.02 mV).

EXAMPLE 3

Figure 6A:
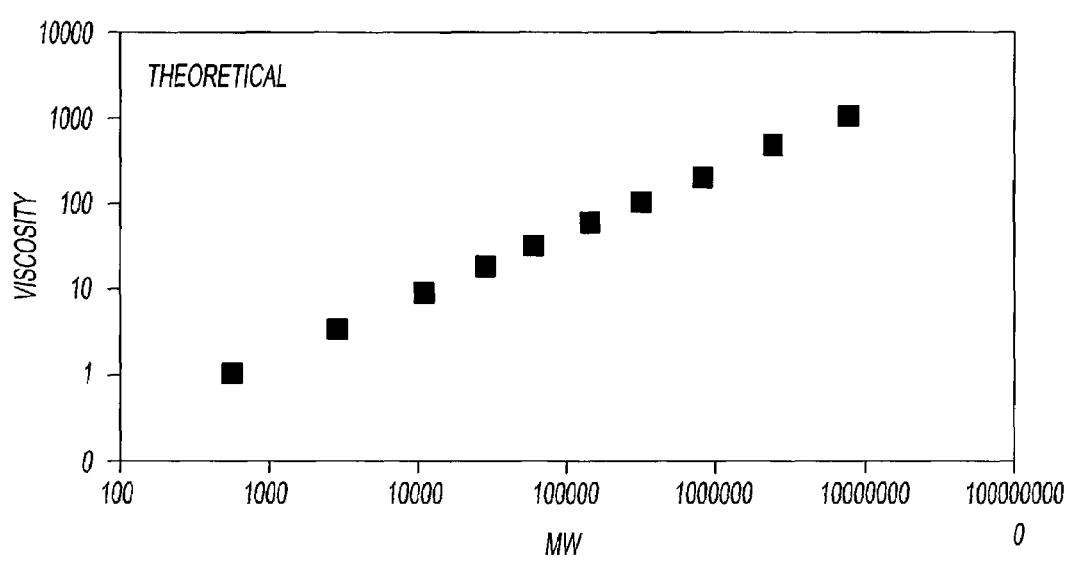
FIGS. 6A and 6B are representative plots obtainable from the use of the present flow detector for sensing viscosity.
Figure 6B:
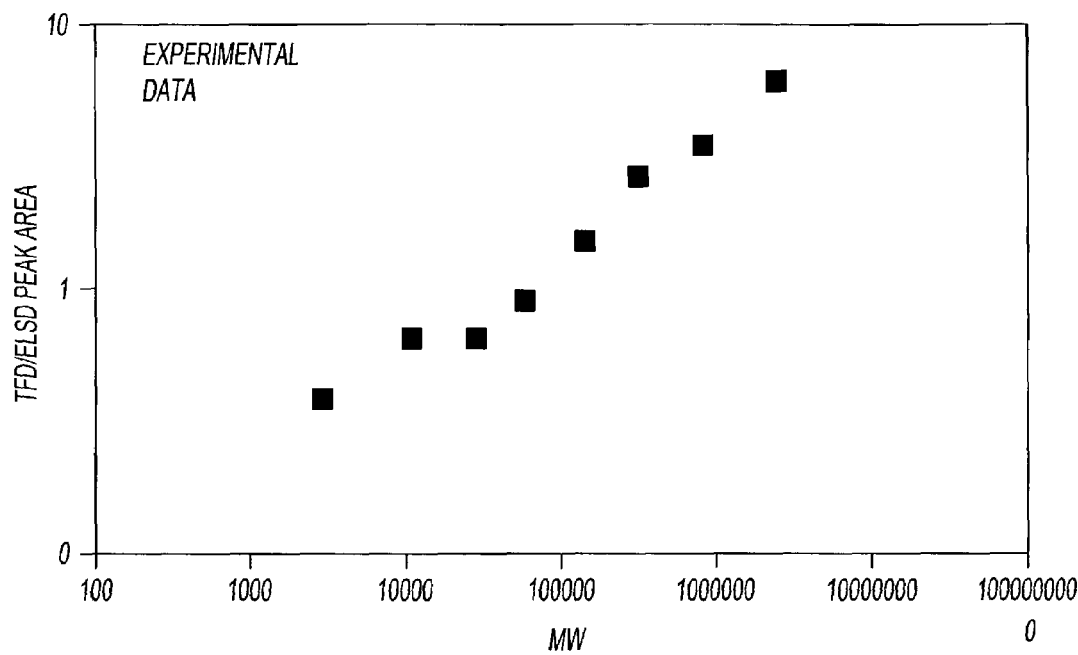

Referring to FIGS. 6A and 6B, there are shown representative plots obtainable from the use of the present flow detector for sensing viscosity. It is known from theory that logarithm of intrinsic viscosity grows linearly with logarithm of molecular weight. Theoretical TFD responses obtained for samples (e.g., polystyrene samples) of different molecular weight in a mobile phase (such as THF, from the experiment described above) are calculated and plotted in FIG. 6A. More specifically, FIG. 6A represents the viscosity-MW (M) relationship as calculated using Mark Houwink equation: $[\eta]=K \times M^{\alpha}$, with the constants for polystyrenes in THF at room temperature taken from the Polymer Handbook ($K=0.011$ mL/g; $[\eta]=0.725$).

The plot of FIG. 6B correlates in similar way the molecular weight with the TFD response normalized for concentration by dividing it with the ELSD response (concentration detector). Linearity of the TFD/ELSD response demonstrates clearly, that the detector of the present invention can be used as a viscosity detector in the range of molecular weight (of polystyrenes) from a few thousands to a couple of millions. Further, deviations from linearity at both low and high-MW ends can be readily explained. Molecular weights of few millions and higher can not be simply sensed because of high frequency needed to achieve a resonance of the tuning fork. Different design of the tuning fork may increase that range towards high-MW polymers further. At the low-MW end, the viscosity effect is being less significant that effect of dielectricity for small molecules and, as a result, TFD works as a universal concentration detector rather than viscosity detector for molecules of MW below one thousand. Constant TFD/ELSD ratio for molecules of the same chemistry but different size suggests that the concentration part of the TTD response is not affected by molecular weight. Therefore, it can be expected that, when viscosity can be expressed directly in terms of molecular weights using Mark-Houwink parameters, the TFD response (TFDR) will generally correspond with concentration and MW in the following fashion:

$$TFD_R = (Constant_1 \times Concentration) + (Constant_2 \times Concentration \times Viscosity).$$

EXAMPLE 4

Figure 7:
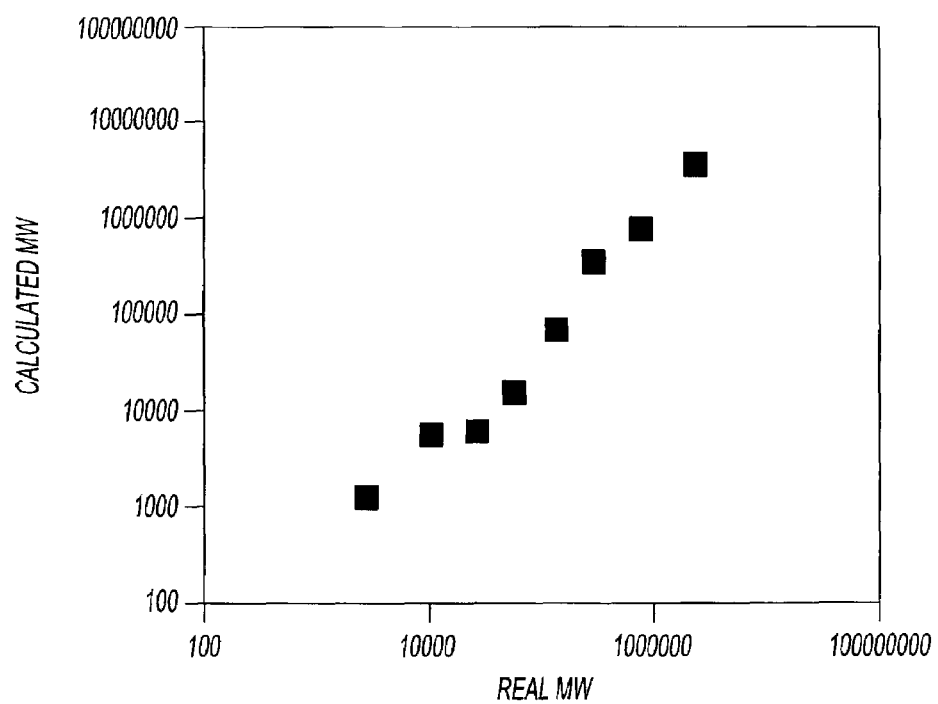
FIG. 7 is a representative plot for calculating molecular weights from a flow detector response in accordance with the present invention.

Referring to FIG. 7, there is illustrated a representative plot for calculating molecular weights from TFD response in accordance with the present invention. Using a simple version of the equation described above allows for a calibration plot as in FIG. 7 that could be used for calculation of molecular weights directly from TFD response by calibrating the system versus concentration signal. There is also a possibility of obtaining the molecular weight information using the TFD only, using two responses at different frequencies or from different tuning forks (possibly in the same cell) varying in the concentration and viscosity portions of the signal.

EXAMPLE 5

Figure 8A:
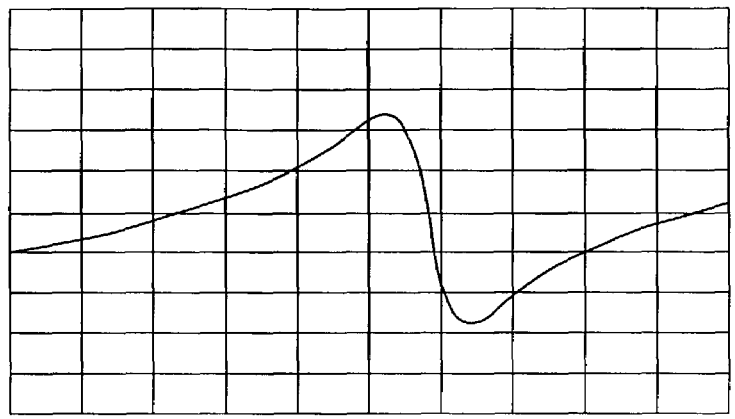
FIGS. 8A-8C are illustrative traces for comparison that are obtainable in accordance with the present invention.
Figure 8B:
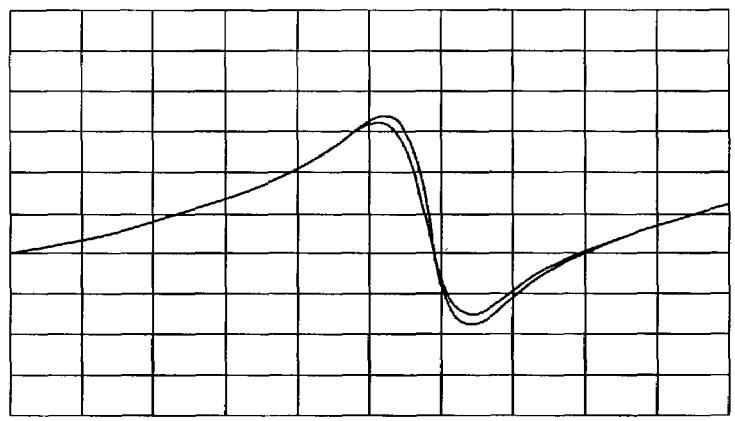
Figure 8C:
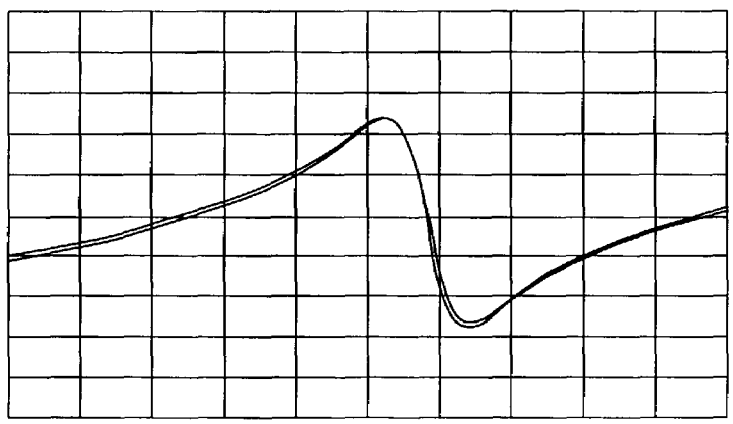

A sample of polystyrene of MW 200k is injected into a stream of THF. Output is shown in FIG. 8A prior to sample flow through the detector, and is shown in FIG. 8C upon conclusion of the experiment. FIG. 8B illustrates representative output during when methanol is passed through the detector cell. The system is equipped with a filter instead of a GPC column and the flow through the detector lasts for about 40 seconds. The outermost trace shown in FIG. 8B is representative of a baseline signal for a pure solvent passing through the detector (which is stored in memory and outputted for comparison as in FIG. 8B). The sample output trace, corresponding with the signal of the flow detector signal during sample flow, is the trace that appears compressed in FIG. 8B. The frequency of resonation was established as 28.1 kHz (the scale of the picture is from 27.0 to 29.0 kHz). As depicted in FIGS. 8A-8C, the shift along the right-left axis represents changes in viscosity.

EXAMPLE 6

Figure 9A:
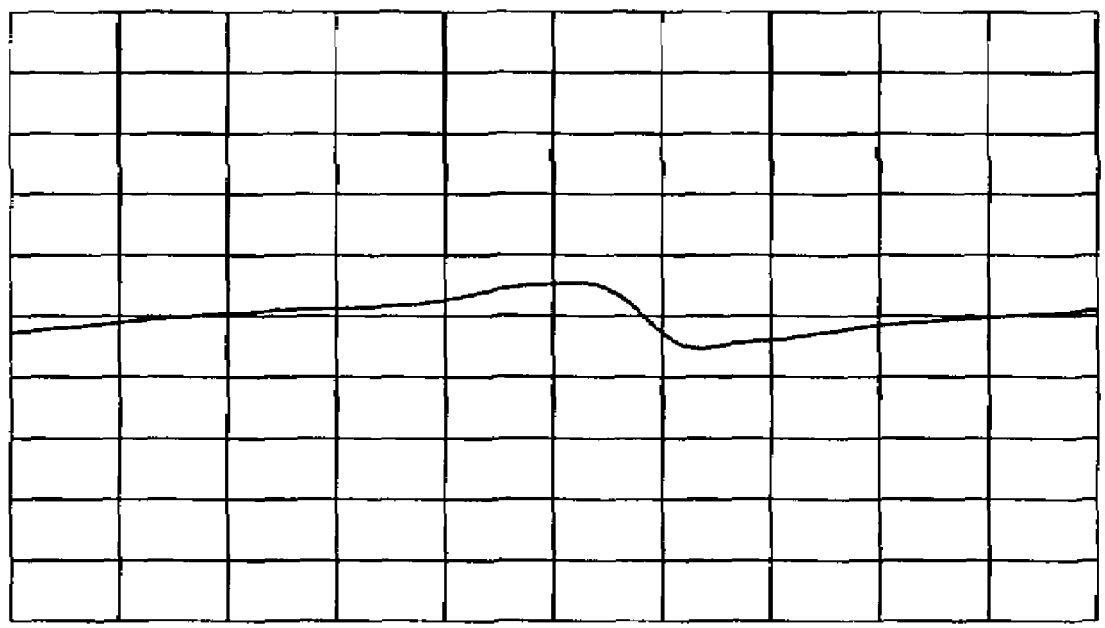
Figure 9B:
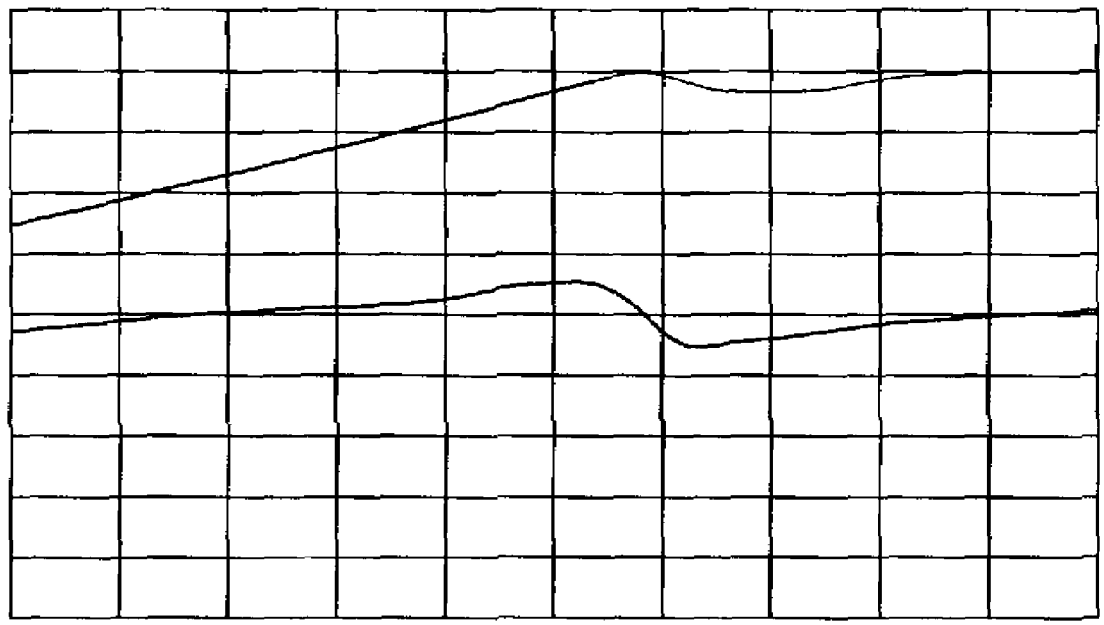

A methanol sample is injected into a stream of THF. Output is shown in FIG. 9A prior to sample flow through the detector, and is shown in FIG. 9C upon conclusion of the experiment. FIG. 9B illustrates representative output during when methanol is passed through the detector cell. The system is equipped with a filter instead of the GPC column and the flow proceeds for about 40 seconds. A distinct upper trace flow detector (corresponding with the detector signal during the experiment) is visible in the output of FIG. 9B, which corresponds with the flow of sample through the detector, as compared with, for instance, the baseline traces of FIG. 9A and 9C (and which is shown for comparison in FIG. 9B, being outputted from memory). The frequency of resonation is established as 28.1 kHz (the scale of the picture is from 27.0 to 29.0 kHz). As depicted in FIGS. 9A-9C, the shift along the up-down axis represents primarily the changes in dielectricity of environment.

EXAMPLE 7

The detector of the present invention is comparable or overperforms premium commercially available viscometric detectors, based upon data that has been published (e.g., chromatographic traces shown), for example at http://www.viscotek.com for comparison. Even without temperature control, measurements using the system of the present invention demonstrate that it can reliable indicate, for a sample of approximately 0.84 M molecular weight of polystyrene with the concentration at the detection point of approximately 0.5 µg/ml (with 5 µg/ml injection for 6 sec and corresponding dilution for approximately 10 times), an intrinsic viscosity is about 5×E-5 from the FIG. 6A, with a dynamic range of at least 100 S/N ratio for the baseline. It puts the sensitivity of the system in the range of the 5 E-7 for the $[\eta]_{sp}$ or 2×E-6 mPa s. If the thermal stability is introduced the intrinsic electrical noise of the system as seen from the detection graph is at least two orders of magnitude better. Therefore the sensitivity of the detector exceeds many application requirements and is very comparable with the most sensitive ELSD detector at present.

EXAMPLE 8

The intrinsic viscosity of polystyrene of 840k molecular weight is 217 mL/g, as obtained by Mark-Houwink equation (FIG. 6A) and the TFD response is at least 100 times of the signal-to-noise ratio (S/N) of the baseline. The concentration at the detection point for that polymer is approximately 0.5 mg/mL (with 5 mg/ml injection for 6 sec and corresponding dilution for approximately 10 times). If three times S/N is considered to be the sensitivity limit, the system is sensitive enough to detect molecules of [η] in the range of 6 mL/g at concentration of 0.5 mg/mL (actual concentration in a detector cell), or polymers of [η] approximately 200 mL/g (like PS 0.8M) at concentration of 0.015 mg/mL. Taking into account the volume of the cell being 15 µL, the sensitivity in terms of total amount of polymer (like PS 800k) possible to detect by TFD is about 0.2 µg. It is noted that the measurable molecular weight range for polystyrenes in THF with the current TFD setup is from about 1k to about 5M, an more preferably about 3k to 3M, with the concentration limit below 1 mg/mL at regular GPC injection volumes of 10-100 µL per column.

Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A tuning fork resonator detector system, comprising:
   an inlet conduit for receiving a fluid sample;
   a head portion including a passageway for defining a detection cell in fluid communication with the inlet conduit;
   a tuning fork resonator including at least one tuning fork, at least a portion of said at least one tuning fork being housed in the passageway;
   an outlet conduit adapted for passage of the sample out of the head portion; and
   an apparatus for performing a non-chromatographic separation of the fluid sample upstream of the head portion.

2. The detector system of claim 1, wherein the inlet conduit and the outlet conduit have cross-sectional areas smaller than a cross sectional area of the head portion.

3. The detector system of claim 1, further comprising a source of a variable frequency input signal for oscillating the tuning fork resonator.

4. A detector for a flow characterization system, comprising:
   an inlet conduit for receiving a fluid sample;
   a detection cell including a flow passageway in fluid communication with the inlet conduit;
   a tuning fork resonator including at least one tuning fork that is operable at a frequency less than about 100 kHz, at least a portion of said at least one tuning fork being located in the flow passageway of the detection cell;
   a housing associated with the detection cell and adapted for connecting the tuning fork resonator with a signal generator, a signal receiver, or a combination thereof; and
   an outlet conduit in fluid communication with the flow passageway of the detection cell;
   wherein the inlet conduit and the outlet conduit are disposed generally orthogonally relative to each other, and
   wherein said at least one tuning fork has tines located in the detection cell in a fluid path between the inlet conduit and the outlet conduit.

5. A tuning fork resonator detector system, comprising:
   a filtration apparatus for performing a non-chromatographic separation of a sample; an inlet for receiving a liquid component of said sample downstream of the filtration apparatus;
   a detection cell in fluid communication with the inlet;
   a tuning fork resonator including at least one tuning fork that is operated at a frequency less than about 100 kHz, at least a portion of said at least one tuning fork being located in the detection cell; and
   an outlet adapted for passage of the liquid component of said sample out of the detection cell;
   wherein said at least one tuning fork has tines located in a fluid path between the inlet and the outlet; and
   wherein the tuning fork resonator is adapted for measuring viscosity of the liquid component of said sample.

6. The detector system of claim 5, further comprising data acquisition hardware in signaling communication with the tuning fork resonator.

7. The detector system of claim 6, further comprising a pump for advancing the liquid component of the sample through the detection cell.

8. The detector system of claim 5, further comprising a pump for advancing the liquid component of the sample through the detection cell.

9. The detector system of claim 5, further comprising a microprocessor in electronic communication with the tuning fork resonator to collect, process and analyze data obtained therefrom.

10. The detector system of claim 7, further comprising a microprocessor in electronic communication with the tuning fork resonator to collect, process and analyze the data obtained therefrom.

11. The detector system of claim 8, wherein the microprocessor also operates the pump.

12. A tuning fork resonator detector system, comprising:
    an inlet conduit for receiving a fluid sample;
    a detection cell including a flow passageway in fluid communication with the inlet conduit;
    a tuning fork resonator comprising at least one tuning fork having tines, at least a portion of said at least one tuning fork being located in the flow passageway of the detection cell; and
    an outlet conduit in fluid communication with the flow passageway of the detection cell for discharging the sample;
    the inlet conduit and the outlet conduit being disposed generally orthogonally relative to each other, and the tuning fork being orientated in the flow passageway such that bulk flow of the fluid sample is substantially parallel to primary surfaces of the tines of the tuning fork.

13. A tuning fork resonator detector system, comprising:
    an inlet conduit for receiving a fluid sample;
    a detection cell including a flow passageway in fluid communication with the inlet conduit;
    a tuning fork resonator, at least a portion of which is located in the flow passageway; and
    an outlet conduit in fluid communication with the flow passageway of the detection cell for discharging the sample;
    the inlet conduit and the outlet conduit being disposed relative to each other, and the tuning fork resonator being orientated in the flow passageway such that the dead volume of the flow passageway of the detection cell is less than about 75 microliters.

14. A tuning fork resonator detector system, comprising:
    an inlet conduit for receiving a fluid sample;
    a detection cell including a flow passageway in fluid communication with the inlet conduit;
    a tuning fork resonator, at least a portion of which is located in the flow passageway; and
    an outlet conduit in fluid communication with the flow passageway of the detection cell for discharging the sample; the inlet conduit and the outlet conduit being disposed at an obtuse angle relative to each other.

15. A tuning fork resonator detector system, comprising:
    an inlet conduit for receiving a fluid sample;

a detection cell including a flow passageway in fluid communication with the inlet conduit;

a tuning fork resonator, at least a portion of which is located in the flow passageway; and an outlet conduit in fluid communication with the flow passageway of the detection cell for discharging the sample;

the detection cell having an internal volume ranging from about 1 microliter to about 500 microliters.

16. A tuning fork resonator detector system, comprising:

an inlet conduit for receiving a fluid sample;

a detection cell including a flow passageway in fluid communication with the inlet conduit;

a tuning fork resonator, at least a portion of which is located in the flow passageway;

an outlet conduit in fluid communication with the flow passageway of the detection cell for discharging the sample;

a library comprising a plurality of fluids, the fluids being spatially separate and addressable for sampling; and an autosampler adapted for sampling the fluids and providing samples of the fluids to the inlet conduit.

17. The tuning fork resonator detector system of claims 15 or 16 wherein the inlet conduit and the outlet conduit are disposed generally orthogonally relative to each other.

18. The tuning fork resonator detector system of claims 13, 14, 15 or 16 wherein the tuning fork resonator comprises at least one tuning fork having tines, the tuning fork being orientated in the flow passageway such that bulk flow of the fluid sample is substantially parallel to primary surfaces of the tines of the tuning fork resonator.

19. The tuning fork resonator detector system of claims 12, 14, 15 or 16 wherein the dead volume of the flow passageway of the detection cell is less than about 75 microliters.

20. The tuning fork resonator detector system of claims 12, 13, 14, 15 or 16 wherein the dead volume of the flow passageway of the detection cell is less than about 50 microliters.

21. The tuning fork resonator detector system of claims 12, 13, 14, 15 or 16 wherein the dead volume of the flow passageway of the detection cell is less than about 20 microliters.

22. The tuning fork resonator detector system of claims 13, 15 or 16 wherein the inlet conduit and the outlet conduit are disposed at an obtuse angle relative to each other.

23. The tuning fork resonator detector system of claims 12, 13, 14 or 16 wherein the detection cell has an internal volume ranging from about 1 microliter to about 500 microliters.

24. The tuning fork resonator detector system of claims 12, 13, 14, 15 or 16 wherein the detection cell has an internal volume ranging from about 5 microliters to about 50 microliters.

25. The tuning fork resonator detector system of claims 12, 13, 14 or 15 further comprising:

a library comprising a plurality of fluids, the fluids being spatially separate and addressable for sampling; and an autosampler adapted for sampling the fluids and providing samples of the fluids to the inlet conduit.

* * * * *